US011992553B2

(12) United States Patent
Nyambura et al.

(10) Patent No.: US 11,992,553 B2
(45) Date of Patent: May 28, 2024

(54) INHALABLE POWDER FORMULATIONS OF ALGINATE OLIGOMERS

(71) Applicant: AlgiPharma AS, Sandvika (NO)

(72) Inventors: Bildad Nyambura, Reading (GB); Anand Bakle, Reading (GB); Arne Dessen, Røyken (NO)

(73) Assignee: AlgiPharma AS, Sandvika (NO)

( * ) Notice: Subject to any disclaimer, the term of this patent is extended or adjusted under 35 U.S.C. 154(b) by 283 days.

(21) Appl. No.: 17/445,577

(22) Filed: Aug. 20, 2021

(65) Prior Publication Data

US 2021/0386666 A1 Dec. 16, 2021

Related U.S. Application Data

(62) Division of application No. 15/507,712, filed as application No. PCT/EP2015/069785 on Aug. 28, 2015, now abandoned.

(51) Int. Cl.
| *A61K 9/16* | (2006.01) |
| *A61K 9/00* | (2006.01) |
| *A61K 9/48* | (2006.01) |
| *A61P 11/00* | (2006.01) |

(52) U.S. Cl.
CPC ............ *A61K 9/0075* (2013.01); *A61K 9/008* (2013.01); *A61K 9/1617* (2013.01); *A61K 9/1623* (2013.01); *A61K 9/1652* (2013.01); *A61K 9/1682* (2013.01); *A61K 9/4808* (2013.01); *A61P 11/00* (2018.01)

(58) Field of Classification Search
None
See application file for complete search history.

(56) References Cited

U.S. PATENT DOCUMENTS

| 5,169,840 | A | 12/1992 | Otterlei et al. |
| 6,121,441 | A | 9/2000 | Simensen et al. |
| 7,258,873 | B2 | 8/2007 | Truong-Le et al. |
| 2012/0065174 | A1 | 3/2012 | Haeberlin et al. |
| 2012/0115803 | A1 | 5/2012 | Onsoyen et al. |
| 2012/0122768 | A1 | 5/2012 | Onsoyen et al. |
| 2012/0321717 | A1 | 12/2012 | Staniforth et al. |

FOREIGN PATENT DOCUMENTS

| CN | 102302477 A | 1/2012 |
| CN | 102458474 A | 5/2012 |
| EP | 2 243 490 A1 | 10/2010 |
| JP | 2003-507412 A | 2/2003 |
| JP | 2012-528840 A | 11/2012 |
| WO | WO 91/11205 A1 | 8/1991 |
| WO | WO 00/33817 A1 | 6/2000 |
| WO | WO 00/45878 A2 | 8/2000 |
| WO | WO 01/13893 A2 | 3/2001 |
| WO | WO 03/045402 A1 | 6/2003 |
| WO | WO 2006/002421 A2 | 1/2006 |
| WO | WO 2007/039754 A1 | 4/2007 |
| WO | WO 2007/039760 A2 | 4/2007 |
| WO | WO 2007/056341 A1 | 5/2007 |
| WO | WO 2007/134279 A2 | 11/2007 |
| WO | WO 2008/125828 A2 | 10/2008 |
| WO | WO 2009/038683 A2 | 3/2009 |
| WO | WO 2009/064959 A1 | 5/2009 |
| WO | WO 2009/068841 A2 | 6/2009 |
| WO | WO 2009/073757 A1 | 6/2009 |
| WO | WO 2009/076141 A2 | 6/2009 |
| WO | WO 2009/076142 A2 | 6/2009 |
| WO | WO 2010/019239 A2 | 2/2010 |
| WO | WO 2010/037066 A2 | 4/2010 |
| WO | WO 2010/048526 A2 | 4/2010 |
| WO | WO 2010/053471 A1 | 5/2010 |
| WO | WO 2010/054138 A2 | 5/2010 |
| WO | WO 2010/138484 A2 | 12/2010 |
| WO | WO 2010/139956 A1 | 12/2010 |
| WO | WO 2011/019413 A1 | 2/2011 |
| WO | WO 2011/050325 A1 | 4/2011 |
| WO | WO2011/072241 A2 | 10/2011 |
| WO | WO 2011/127241 A2 | 10/2011 |

(Continued)

OTHER PUBLICATIONS

Chow, et al. 2007 "Particle Engineering for Pulmonary Drug Delivery" *Pharmaceutical Research* 24(3):411-437.
Derichs 2013 "Targeting a genetic defect: cystic fibrosis transmembrane conductance regulator modulators in cystic fibrosis" *Eur Respir Rev* 22(127): 58-65.
Pedemonte, et al. 2005 "Phenylglycine and Sulfonamide Correctors of Defective ΔF508 and G551D Cystic Fibrosis Transmembrane Conductance Regulator Chloride-Channel Gating" *Molecular Pharmacology* 67(5): 1797-1807.
Pedemonte, et al. 2005 "Small-molecule correctors of defective ΔF508-CFTR cellular processing identified by high-throughput screening" *J Clin Invest* 115(9): 2564-2571.
Pettit & Fellner 2014 "CFTR Modulators for the Treatment of Cystic Fibrosis" *Pharmacy and Therapeutics* 39(7): 500-511.

(Continued)

*Primary Examiner* — Celeste A Roney
(74) *Attorney, Agent, or Firm* — Knobbe, Martens, Olson & Bear, LLP

(57) ABSTRACT

A method of preparing spray dried particles for inhalation comprising providing: (i) an aqueous liquid composition including the alginate oligomer and an aqueous liquid composition including an anti-adherent compound, or (ii) an aqueous liquid composition including the alginate oligomer and an anti-adherent compound; providing an organic liquid composition including a phospholipid; combining a volume of the organic liquid composition with a volume of the aqueous liquid composition, wherein the total volume of the organic liquid composition is smaller than the total volume of the aqueous liquid composition with which it is combined, and wherein the total volume of aqueous liquid composition and said total volume of organic liquid composition are sufficient to provide a combination; homogenizing the combination to form an organic-in-aqueous liquid emulsion for spray drying; and spray drying the organic-in-aqueous liquid emulsion to form the spray dried particles for inhalation.

29 Claims, 5 Drawing Sheets

(56) References Cited

FOREIGN PATENT DOCUMENTS

| WO | WO 2011/127290 A2 | 10/2011 |
|----|-------------------|---------|
| WO | WO 2011/133751 A2 | 10/2011 |
| WO | WO 2011/133951 A1 | 10/2011 |
| WO | WO 2011/133953 A1 | 10/2011 |
| WO | WO 2011/133956 A1 | 10/2011 |
| WO | WO 2011/146901 A1 | 11/2011 |
| WO | WO 2013/164380 A1 | 11/2013 |
| WO | WO 2015/128495 A1 | 9/2015  |

OTHER PUBLICATIONS

Van Goor, et al. 2005 "Rescue of ΔF508-CFTR trafficking and gating in human cystic fibrosis airway primary cultures by small molecules" *Am J Physiol Lung Cell Mol Physiol* 290: L1117-L1130.

Vehring 2007 "Pharmaceutical Particle Engineering *via* Spray Drying" *Pharmaceutical Research* 25(5): 999-1022.

Yang, Xiao-bo, et al., "Optimization and Characterization of Dry Powder of Fanhuncaoin for Inhalation Based on Selection of Excipients," *Chem. Pharm. Bull.* 59(8) 929-937 (Aug. 2011).

Nordgård et al., "Oligosaccharides as Modulators of Rheology in Complex Mucous Systems", Biomacromolecules, 12(8), pp. 3084-3090, Jun. 18, 2011.

A

B

C

D

A

B

C

D

INHALABLE POWDER FORMULATIONS OF ALGINATE OLIGOMERS

FIELD

The present invention relates to novel formulations of alginate oligomers that are especially suited for inhalation routes of administration. More specifically, the present invention provides spray dried particles for inhalation in dry powder form containing a high proportion of alginate oligomer, a phospholipid and an anti-adherent compound. The uncomplicated formulation of the invention provides particles with a fine particle mass (FPM), geometric particle size distribution and emitted dose that permits effective delivery of the alginate oligomer to the lungs of a subject undergoing treatment with minimised risk of adverse reaction to excipients. The invention further provides dry powder compositions for inhalation containing the spray dried particles, capsules containing said particles and dry powder inhalers containing said particles. The invention further provides a surprising and advantageous method for preparing the particles of the invention in which an organic-in-aqueous liquid emulsion of the alginate oligomer, the phospholipid and the anti-adherent compound is prepared and said emulsion is spray dried. The use of the particles of the invention in therapy, in particular the treatment or prevention of respiratory infections and respiratory disorders is provided, especially disorders or conditions which involve microbial infection, in particular biofilm infection, and/or abnormal mucus, e.g. COPD, COAD, COAP, bronchitis, cystic fibrosis, a medical disorder or condition associated with CF, emphysema, lung cancer, asthma or pneumonia, or more broadly any condition associated with or characterised by defective cystic fibrosis transmembrane conductance regulator (CFTR) ion channel function.

BACKGROUND

Alginate oligomers have been described in the literature at length. Briefly, alginates are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate). Alginate oligomers may be obtained from alginate polymers which are typically isolated from natural sources as large high molecular weight polymers (e.g. an average molecular weight in the range 300,000 to 500,000 Daltons). Such large alginate polymers may be degraded, or broken down, e.g. by chemical or enzymatic hydrolysis to produce alginate structures of lower molecular weight.

Alginate oligomers have been shown to be able to reduce the viscosity of mucus, in particular hyperviscous mucus, to have antimicrobial properties and also antibiofilm properties. Their use in the treatment or prevention of respiratory infections and respiratory disorders in which microbial infection, in particular biofilm infection and/or abnormal mucus are involved, e.g. COPD, COAD, COAP, bronchitis, cystic fibrosis, a medical disorder or condition associated with CF, emphysema, lung cancer, asthma and pneumonia have therefore been suggested, amongst others.

Effective delivery of active agents, especially complex biomolecules such as alginate oligomers, to the lungs can be difficult to achieve and idiosyncratic. Many alternatives are available from the art. Accordingly, a proposal to deliver an active agent to the lungs may not be as straightforward as first appears. To date little specific direction as to the effective delivery of appropriate doses of alginate oligomers to the lungs has been given in the literature and, in particular, the preparation of a dry powder form of an alginate oligomer has not been described.

SUMMARY

It has now been found that alginate oligomers cannot be successfully formulated as pure dry powders with a fine particle mass (FPM), geometric particle size distribution and emitted dose that permit effective delivery of the alginate oligomer to the lungs. It has however surprisingly been found that when the alginate oligomer is combined with relatively small amounts of a phospholipid and an anti-adherent compound, particles can be prepared by spray drying which have a fine particle mass (FPM), geometric particle size distribution and emitted dose that permit effective delivery of the alginate oligomer to the lungs. Without wishing to be bound by theory, the surfactant properties of the phospholipid are believed to enable a partial masking of the alginate oligomer in the spray dried powder, reducing the hydrophilicity and thereby the hygroscopic nature of the powder. This is further believed to lead to the desired size distribution and to reduce deposition in the mouth and trachea rather than the lungs, thereby increasing bioavailability in the lungs.

Thus in a first aspect there is provided spray dried particles for inhalation, said particles consisting of
  (i) at least about 70% w/w of an alginate oligomer,
  (ii) at least about 10% w/w in total of a phospholipid and an anti-adherent compound, wherein said phospholipid is solid at room temperature, and wherein said phospholipid is present at no less than 0.5% w/w and said anti-adherent compound is present at no less than 0.5% w/w, and
  (iii) no greater than about 10% w/w of further excipients.

In preferred embodiments the particles of the invention contain at least about 71% w/w of the alginate oligomer, e.g. at least about 72, 73, 74, 75, 76, 77, 78, 79, 80, 81, 82, 83, 84, 85, 86, 87, 88, 89 or 90% w/w of the alginate oligomer. In other preferred embodiments the particles of the invention contain about 70% to about 90% w/w of the alginate oligomer, e.g. any one of about 71, 72, 73, 74, 75, 76, 77, 78, 79, 80% w/w to any one of about 81, 82, 83, 84, 85, 86, 87, 88, 89 or 90% w/w of the alginate oligomer, e.g. 72-88, 74-86, 75-85, 76-84, 77-83, 78-82, 79-81, 74-90, 75-89, 76-88, 77-87, 78-86, 79-85, 80-84, 81-83, 78-90, 79-89, 80-88, 81-87, 82-86, 83-85, 80-90, 81-89, 82-88, 83-87 or 84-86% w/w. Preferably the particles of the invention contain about 80% w/w of the alginate oligomer, e.g. 78, 79, 80, 81 or 82% w/w, preferably 79, 80 or 81% w/w, more preferably 80% w/w.

In preferred embodiments the particles of the invention contain at least about 11% w/w in total of the phospholipid and the anti-adherent compound, e.g. at least about 12, 13, 14, 15, 16, 17, 18, 19, 20, 21, 22, 23, 24, 25, 26, 27, 28, 29 or 30% w/w in total of the phospholipid and the anti-adherent compound. In other preferred embodiments the particles of the invention contain about 10% to about 30% w/w in total of the phospholipid and the anti-adherent compound, e.g. any one of about 11, 12, 13, 14, 15, 16, 17, 18, 19, 20% w/w to any one of about 21, 22, 23, 24, 25, 26, 27, 28, 29 or 30% w/w in total of the phospholipid and the anti-adherent compound, e.g. 12-28, 14-26, 15-25, 16-24, 17-23, 18-22, 19-21, 14-30, 15-29, 16-28, 17-27, 18-26, 19-25, 20-24, 21-23, 18-30, 19-29, 20-28, 21-27, 22-26, 23-25, 20-30, 21-29, 22-28, 23-27 or 24-26% w/w. Preferably the particles of the invention contain about 20% w/w in total of the phospholipid and the anti-adherent compound, e.g. 18, 19, 20, 21 or 22% w/w, preferably 19, 20 or 21% w/w, more preferably 20% w/w.

BRIEF DESCRIPTION OF THE DRAWINGS

The invention will be further described with reference to the following non-limiting Examples in which.

DETAILED DESCRIPTION

Figure 1:
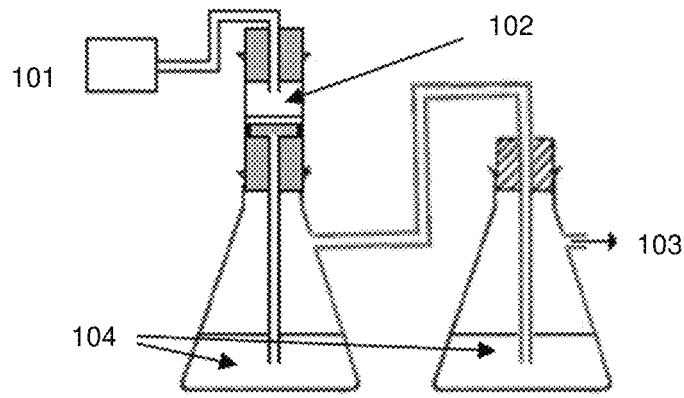
FIG. 1 shows a diagram of the apparatus used to radiolabel spray dried particles of the invention with Technegas. Technegas was generated by a Technegas Generator loaded with $^{99m}$pertechnetate (400 Mbq) [101] and was drawn over a bed of dry particles (300 mg) arranged on filter paper [102] using a vacuum pump [103]. Free Technegas was trapped in 6% (w/w) EDTA solution [104].

Within the constraints of the aforementioned preferred embodiments the particles of the invention contain no less than 0.5% w/w of the phospholipid, e.g., no less than 1, 2, 3, 4, 5, 6, 7, 8, 9, 10, 11, 12, 14, 16, 18, 20, 25 or 29.5% w/w. In preferred embodiments the particles of the invention contain 0.5-15% w/w of the phospholipid, e.g. 1-9, 2-8, 3-7, 4-6, 2-9, 3-8, 4-7, 5-6, 3-9, 4-8, 5-7, 4-9, 5-8, 6-7, 5-9, 6-8, 1-10, 1-11, 1-12, 2-10, 2-11, 2-12, 3-10, 3-11, 3-12, 4-10, 4-11, 5-12, 5-10, 5-11, 5-12, 6-10, 6-11, 6-12, 7-10, 7-11, 7-12 or 8-10, 8-11, 8-12% w/w. Preferably the particles of the invention contain about 5% w/w of the phospholipid, e.g. 3, 4, 5, 6 or 7% w/w, preferably 4, 5 or 6% w/w, more preferably 5% w/w.

Within the constraints of the aforementioned preferred embodiments the particles of the invention contain no less than 0.5% w/w of the anti-adherent compound, e.g. no less than 1, 2, 3, 4, 5, 6, 7, 8, 9, 10, 11, 12, 14, 16, 18, 20, 25 or 29.5% w/w. In preferred embodiments the particles of the invention contain than 0.5-20% w/w of the anti-adherent compound, e.g. 1-19, 2-18, 3-17, 4-16, 5-15, 6-14, 7-13, 2-19, 3-18, 4-17, 5-16, 6-15, 7-14, 8-13, 3-19, 4-18, 5-17, 6-16, 7-15, 8-14, 9-13, 4-19, 5-18, 6-17, 7-16, 8-15, 9-13, 5-19, 6-18, 7-17, 8-16, 9-15, 1-14, 1-15, 1-16, 2-14, 2-15, 2-16, 3-14, 3-15, 3-16, 4-14, 4-15, 5-14, 6-14, 7-11, 7-12 or 8-10, 8-11, 8-12% w/w. Preferably the particles of the invention contain about 15% w/w of the anti-adherent compound, e.g. 13, 14, 15, 16 or 17% w/w, preferably 14, 15 or 16% w/w, more preferably 15% w/w.

In further preferred embodiments the particles of the invention contain about 5% w/w of the phospholipid, e.g. 3, 4, 5, 6 or 7% w/w, preferably 4, 5 or 6% w/w, more preferably 5% w/w and about 15% w/w of the anti-adherent compound, e.g. 13, 14, 15, 16 or 17% w/w, preferably 14, 15 or 16% w/w, more preferably 15% w/w. More preferably the particles of the invention contain about 5% w/w of the phospholipid and about 15% w/w of the anti-adherent compound.

In other embodiments the relative amounts of phospholipid and anti-adherent compound present in the particles are in a ratio of 1:5 to 5:1, preferably 1:4.5 to 4.5:1, 1:4 to 4:1, 1:3.5 to 3.5:1, 1:3 to 3:1, 1:2.5 to 2.5:1, 1:2 to 2:1, 1:1.5 to 1.5:1 or 1:1, more preferably 1:3.5, 1:3 or 1:2.5, most preferably 1:3.

In other embodiments the relative amounts of the alginate oligomer and the combined amounts of phospholipid and anti-adherent compound present in the particles are in a ratio of 7:3, 7:2.5, 7:2, 7.5:2.5, 7.5:1.5, 8:2, 8:1.5, 8:1, 8.5:1.5, 8.5:1 or 9:1.

In other embodiments the relative amounts of the alginate oligomer, the phospholipid and anti-adherent compound present in the particles are in a ratio of 7:2:1, 7:1.5:1.5, 7:1:2, 7:0.5:2.5, 7:0.05:2.95, 8:1.5:0.5, 8:1:1, 8:0.5:1.5, 8:0.05:1.95, 9:0.75:0.25, 9:0.5:0.5, 9:0.25:0.75, or 9:0.5:0.95, 8:0.5:1.5 is preferred. Preferably in these embodiments no further excipients are present In preferred embodiments the particles of the invention contain no greater than about 9% w/w of further excipients, e.g. no greater than about 8, 7, 6, 5, 4, 3, 2, 1, 0.5, 0.1, 0.05, 0.01, 0.005 or 0.001% w/w of further excipients. In most preferred embodiments the particles of the invention contain essentially no further excipients. Suitable further excipients are disclosed herein. In certain embodiments a further excipient is not a phospholipid, e.g. those which are solid at room temperature, or an anti-adherent compound.

In one embodiment the particles of the invention contain about 80% w/w alginate oligomer, about 15% w/w anti-adherent compound and about 5% w/w phospholipid and essentially no further excipients.

For the avoidance of doubt, in this aspect of the invention the sum of the individual percentage amounts of each component will be 100%. It may be that upon preparation the particles of the invention retain solvent molecules, e.g. water molecules, in intimate association with the molecules of alginate oligomer, phospholipid, anti-adherent compound and/or further excipient. For the purposes of the present invention residual solvent associated in this way is included pro rata in the % w/w calculations and so has no impact on relative amounts of the components of particles of the invention.

"% w/w" (or "percentage weight by weight") is a commonly used expression designating the proportion of a solid composition that is made up of the compound in question. 1% w/w equates to 1 gram of compound per 100 grams of solid composition, 2% w/w equates to 2 g of compound per 100 g of solid composition, and so on. 1% w/w also equates to 10 gram of compound per kilogram of solid composition.

The particles of the invention permit effective delivery of the alginate oligomer to the lungs of a subject undergoing treatment.

As noted above, a particular feature of the particles of the invention is that they are of a size appropriate, or suitable, for inhalation, that is for delivery to the lungs of a subject by means of a dry powder inhaler (i.e. an inhaler device suitable for administration of a powder). More specifically, the particles have an aerodynamic particle size of less than 5 µm, for example up to 4.9, 4.8, 4.7, 4.6, or 4.5 µm. Alternatively expressed, the particles have a mass median aerodynamic diameter (MMAD) of less than 5 µm, e.g. up to 4.9, 4.8, 4.7, 4.6, or 4.5 µm. In particular, the particles advantageously have a uniform, or substantially uniform, size distribution, i.e. they are substantially homogenous or monodisperse. Thus, the particles have a relatively narrow aerodynamic particle size distribution (APSD). APSD may be defined with reference to the fine particle mass (FPM), as defined further below. Preferably, the particles are readily aerosolizable at relatively low aerodynamic dispersion forces.

The particles of the invention preferably have a geometric particle size distribution that is acceptable for inhalation, i.e. a d50 of <5 µm and a d90 of <10 µm and preferably a d10 of <1.5 µm as measured in accordance with the protocol of the Examples, i.e. as measured using a Malvern Mastersizer MicroPlus particle size analyer (Malvern Instruments, UK) following dispersion of 15 mg particles in 3 ml of ethyl acetate containing sorbitane trioleate (SPAN 85) at a concentration of 2 g/l.

In certain embodiments the particles of the invention may a d50 of <4 µm or <3 or <2.5 µm. In other embodiments the particles of the invention may have a d50 of about or approximately 3 µm, e.g. a d50 of 2-4, 2.5-4.0, 2.5-3.8, 2.5-3.5, 2.8-3.8, 2.8-3.5, or 2.8-3.2 µm.

In other embodiments the particles of the invention may a d90 of <8 µm or <7 or <6 µm.

In other embodiments the particles of the invention may a d10 of <2 µm or <1 or <0.5 µm.

Any and all combinations of d10, d50 and/or d90 are contemplated, although in certain embodiments the particles may be described by reference to only a single d parameter, e.g. a d50 of <5 µm or a d50 of <3 µm. In another embodiment the particles of the invention may have a d50 of ~3 µm. The particles of the invention preferably have a FPM (size distribution <4.46 µm) of greater than about 10 mg, e.g. 11, 12, 13, 14, 15, 16, 17, 18, 19 or 20 mg per 40 mg of particles as measured in accordance with the protocol of the Examples, i.e. as determined using a next generation impactor (NGI) and a high resistance (60 L) Plastiape monodose device as the particle delivery means. This may be expressed as a percentage $FPM_{<4.46\mu m}$ of greater than about 25%, e.g. 28%, 30%, 33%, 35%, 38%, 40%, 43%, 45%, 48%, or 50%.

The particles of the invention preferably have an emitted dose of greater than about 65%, e.g. 66, 67, 68, 69, 70, 71, 72, 73, 74, 75, 76, 77, 78, 79 or 80% as measured in accordance with the protocol of the Examples, i.e. as determined using a next generation impactor (NGI) and a high resistance (60 L) Plastiape monodose device as the particle delivery means.

The particles of the invention preferably display at least about 90%, e.g. at least 91, 92, 93, 94, 95, 96, 97, 98 or 99% release of alginate oligomer upon exposure of 4 mg of particles to at least 0.1 ml saline for at least one hour at room temperature.

As noted above, alginates typically occur as polymers of an average molecular mass of at least 35,000 Daltons, i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. An alginate oligomer can be considered to be an alginate of an average molecular weight of less than 35,000 Daltons (i.e. less than approximately 190 or less than approximately 175 monomer residues), in particular an alginate of an average molecular weight of less than 30,000 Daltons (i.e. less than approximately 175 or less than approximately 150 monomer residues) more particularly an average molecular weight of less than 25,000 or 20,000 Daltons (i.e. less than approximately 135 or 125 monomer residues or less than approximately 110 or 100 monomer residues).

Viewed alternatively, an oligomer generally comprises 2 or more units or residues and an alginate oligomer for use according to the invention will typically contain 2 to 100 monomer residues, more typically 3, 4, 5 or 6 to 100, and may contain 2, 3, 4, 5 or 6 to 75, 2, 3, 4, 5 or 6 to 50, 2, 3, 4, 5 or 6 to 40, 2, 3, 4, 5 or 6 to 35 or 2, 3, 4, 5 or 6 to 30 residues. Thus, an alginate oligomer for use according to the invention will typically have an average molecular weight of 350, 550, 700, 900 or 1000 to 20,000 Daltons, 350, 550, 700, 900 or 1000 to 15,000 Daltons, 350, 550, 700, 900 or 1000 to 10,000 Daltons, 350, 550, 700, 900 or 1000 to 8000 Daltons, 350, 550, 700, 900 or 1000 to 7000 Daltons, or 350, 550, 700, 900 or 1000 to 6,000 Daltons.

Alternatively put, the alginate oligomer may have a degree of polymerisation (DP), or a number average degree of polymerisation (DPn) of 2 to 100, preferably 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or

DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, e.g. a 5- to 20-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons or 900 to 3500 Daltons. Other representative alginate oligomers include, as mentioned above, oligomers with 5, 6, 7, 8, 9, 10, 11, 12 or 13 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5-18 or 7-15 or 8-12, especially 10.

The alginate oligomer of the invention may have a degree of polymerisation (DP), or a number average degree of polymerisation ($DP_n$), of 3-24, 4-23, 5-22, 6-21, 7-20, 8-19, 9-18, 10-17, 11-16, 12-15 or 13-14 (e.g. 13 or 14).

The alginate oligomer of the invention may have a degree of polymerisation (DP), or a number average degree of polymerisation (DPn), of 4-25, 5-24, 6-23, 7-22, 8-21, 9-20, 10-19, 11-18, 12-17, 13-16, 14-15 (e.g. 14 or 15).

The alginate oligomer of the invention may have a degree of polymerisation (DP), or a number average degree of polymerisation ($DP_n$), of 5-26, 6-25, 7-24, 8-23, 9-22, 10-21, 11-20, 12-19, 13-18, 14-17 or 15-16 (e.g. 15 or 16).

The alginate oligomer of the invention may have a degree of polymerisation (DP), or a number average degree of polymerisation ($DP_n$), of 4-50, 4-40, 4-35, 4-30, 4-28, 4-26, 4-22, 4-20, 4-18, 4-16 or 4-14.

The alginate oligomer of the invention may have a degree of polymerisation (DP), or a number average degree of polymerisation ($DP_n$), of 5-50, 5-40, 5-25, 5-22, 5-20, 5-18, 5-23, 5-20, 5-18, 5-16 or 5-14.

The alginate oligomer of the invention may have a degree of polymerisation (DP), or a number average degree of polymerisation ($DP_n$), of 6-50, 6-40, 6-35, 6-30, 6-28, 6-26, 6-24, 6-20, 6-19, 6-18, 6-16 or 6-14.

The alginate oligomer of the invention may have a degree of polymerisation (DP), or a number average degree of polymerisation ($DP_n$), of 8-50, 8-40, 8-35, 8-30, 8-28, 8-25, 8-22, 8-20, 8-18, 8-16 or 8-14.

The alginate oligomer of the invention may have a degree of polymerisation (DP), or a number average degree of polymerisation ($DP_n$), of 9-50, 9-40, 9-35, 9-30, 9-28, 9-25, 9-22, 9-20, 9-18, 9-16 or 9-14.

The alginate oligomer of the invention may have a degree of polymerisation (DP), or a number average degree of polymerisation ($DP_n$), of 10-50, 10-40, 10-35, 10-30, 10-28, 10-25, 10-22, 10-20, 10-18, 10-16 or 10-14.

The alginate oligomer of the invention may have a degree of polymerisation (DP), or a number average degree of polymerisation ($DP_n$), of 11-50, 11-40, 11-35, 11-30, 11-28, 11-25, 11-22, 11-20, 11-18, 11-16 or 11-14.

The alginate oligomer of the invention may have a degree of polymerisation (DP), or a number average degree of polymerisation ($DP_n$), of 12-50, 12-40, 12-35, 12-30, 12-28, 12-25, 12-22, 12-20, 12-18, 12-16 or 12-14.

The alginate oligomer of the invention may have a degree of polymerisation (DP), or a number average degree of polymerisation ($DP_n$), of 13-50, 13-40, 13-35, 13-30, 13-28, 13-25, 13-22, 13-20, 13-18, 13-16 or 13-14.

The alginate oligomer of the invention may have a degree of polymerisation (DP), or a number average degree of polymerisation ($DP_n$), of 14-50, 14-40, 14-35, 14-30, 14-28, 14-25, 14-22, 14-20, 14-18, 14-16 or 14-15.

The alginate oligomer of the invention may have a degree of polymerisation (DP), or a number average degree of polymerisation ($DP_n$), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation ($DP_n$), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for $DP_n$. Likewise it is preferred that no more than 10%, preferably no more than 9, 8, 7, 6, 5, 4, 3, 2, or 1% mole has a DP below a number three, two or one smaller than the relevant lower limit for $DP_n$.

Suitable alginate oligomers are described in WO2007/039754, WO2007/039760, WO 2008/125828, and WO2009/068841, the disclosures of which are explicitly incorporated by reference herein in their entirety.

Representative suitable alginate oligomers have a $DP_n$ in the range 5 to 30, a guluronate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate fraction ($F_G$) of at least 0.92, a mannuronate fraction ($F_M$) of no more than 0.08, and having at least 95% mole with a degree of polymerization less than 17.

Further suitable alginate oligomers have a number average degree of polymerization in the range 5 to 20, a guluronate fraction ($F_G$) of at least 0.85 and a mannuronate fraction ($F_M$) of no more than 0.15.

Further suitable alginate oligomers have a number average degree of polymerization in the range 5 to 20, a guluronate fraction ($F_G$) of 0.9-0.95 and a mannuronate fraction ($F_M$) of 0.05-0.1, which may be expressed as an alginate oligomer having 90-95% G residues and an average molecular weight of 2600 Da. Further suitable alginate oligomers have a number average degree of polymerization about 13 (e.g. 12, 13 or 14), a guluronate fraction ($F_G$) of at least about 0.80, 0.85, 0.87, 0.88, 0.90 or 0.93 (e.g. 0.92, 0.93 or 0.94) and a corresponding mannuronate fraction ($F_M$) of no more than about 0.20, 0.15, 0.13, 0.12, 0.10, or 0.07 (e.g. 0.08, 0.07 or 0.06).

Further suitable alginate oligomers have a number average degree of polymerization about 21 (e.g. 20, 21 or 22), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

Further suitable alginate oligomers have a number average degree of polymerization about 6 (e.g. 5, 6 or 7), a guluronate fraction ($F_G$) of at least about 0.80 (e.g. 0.85, 0.87, 0.88, 0.90, 0.92, 0.94 or 0.95) and a corresponding mannuronate fraction ($F_M$) of no more than about 0.20 (e.g. 0.15, 0.13, 0.12, 0.10, 0.08, 0.06, 0.05).

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment at least, or more particularly more than, 50% of the monomer residues of the alginate oligomer may be M residues (i.e. mannuronate or mannuronic acid). In other words the alginate oligomer will contain at least or alternatively more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

In certain embodiments the terminal uronic acid residues of the oligomers of the invention do not have a double bond, especially a double bond situated between the $C_4$ and $C_5$ atom. Such oligomers may be described as having saturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers on the invention. In other embodiments enzymatic digestion is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Florida, USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigresens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may be more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvåg et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than AlgE4 is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra).

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to treat or prevent a respiratory infection or a respiratory disorder, especially disorders or conditions which involve microbial infection, in particular biofilm infection, and/or abnormal mucus, e.g. any condition associated with or characterised by defective CFTR ion channel function, COPD, COAD, COAP, bronchitis, cystic fibrosis, a medical disorder or condition associated with CF, emphysema, lung cancer, asthma or pneumonia, that is substantially lower than that of the unmodified oligomer. Common saccharide modifying groups would include acetyl, sulphate, amino, deoxy, alcohol, aldehyde, ketone, ester and anhydro groups. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The invention encompasses the use of a single alginate oligomer or a mixture (multiplicity/plurality) of different alginate oligomers. Thus, for example, a combination of different alginate oligomers (e.g. two or more) may be used.

The phospholipids of use in the invention are those which, when in a pure form, are solid at room temperature (about 20° C.) and at standard atmospheric pressure (1 atm; approximately 101325 Pa). Representative examples include, but are not limited to, phosphatidylcholines, phosphatidylethanolamines, phosphatidylglycerols, phosphatidylserines, phosphatidylinositols and combinations thereof, e.g. phosphatidyl choline (saturated and unsaturated), phosphatidyl ethanol amine, phosphatidyl glycerol, phosphatidyl serine, phosphatidyl inositol, dioleoylphosphatidylcholine, dimyristoyl phosphatidylcholine, dipalmitoylphosphatidylcholine (DPPC; 1,2-Dipalmitoyl-snglycero-3-phosphocholine), distearoyl phosphatidylcholine, 1,2-Distearoyl-sn-glycero-3-phosphocholine (DSPC), diarachidoyl phosphatidylcholine, dibenoyl phosphatidylcholine, ditricosanoyl phosphatidylcholine, dilignoceroylphatidylcholine, dimiristoylphosphatidylethanolamine, dipalmitoyl-phosphatidylethanoalamine, pipalmitoleoylphosphatidylethanolamine, distearoyl-phosphatidylethanolamine, dimyristoylphosphatidylglycerol, dipalmitoylphosphatidyl glycerol, dipalmitolcoylphosphatidylglycerol and hydrogenated derivatives. DPPC and DSPC are preferred as these compounds are found naturally in the lungs. DPPC is especially preferred. Multiple different phospholipids may be used.

The term "anti-adherent compound" is used herein in its usual sense in the field of DPI formulations, i.e. a compound which combats adherence between particles thus preventing particle agglomeration. It will be readily understood however that the anti-adherent compound of the particles of the invention is not a phospholipid as described herein.

Multiple different anti-adherent compounds may be used. The anti-adherent compound may be an amino acid, e.g. a hydrophobic amino acid, in any isomeric form e.g. L- or D-. Amino acids will be well tolerated by subjects undergoing treatment in accordance with the invention. Representative examples include but are not limited to histidine, alanine, isoleucine, arginine, leucine, asparagine, lysine, aspartic acid, methionine, cysteine, phenylalanine, glutamic acid, threonine, glutamine, tryptophan, glycine, valine, ornithine, proline, selenocysteine, serine, and tyrosine, e.g. glycine, lysine, proline, alanine, cysteine, methionine, valine, leucine, tyrosine, isoleucine, phenylalanine, tryptophan. Preferred amino acids include leucine, isoleucine, alanine, valine, phenylalanine, lysine and glycine, e.g. leucine, lysine and glycine, in particular glycine. Combinations of amino acids can also be employed, e.g. glycine and leucine. Furthermore, combinations of hydrophobic and hydrophilic (preferentially partitioning in water) amino acids, where the overall combination is hydrophobic, can also be employed.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term "hydrophobic amino acid" refers to an amino acid that, on the hydrophobicity scale has a value greater than or equal to 0.5, in other words, has a tendency to partition in a nonpolar solvent which is at least equal to that of glycine.

Other anti-adherent compounds include mono- and disaccharides. The monosaccharide or one or more of the monosaccharide residues of the disaccharide may be a triose, a tetrose, a pentose, a hexose, a heptose, an octose, a nonose or a decose in pyranose or furanose form and/or L- or D-form where appropriate and/or sugar derivatives thereof. Pentose or hexose saccharides/residues are preferred, e.g. mannose (e.g. D-mannose), galactose (e.g. D-galactose), glucose (e.g. D-glucose), fructose, fucose (e.g. L-fucose), N-acetyl-glucosamine, N-acetylgalactosamine, rhamnose, galactosamine, glucosamine (e.g. D-glucosamine), galacturonic acid, glucuronic acid, N-acetylneuraminic acid, methyl D-mannopyranoside (mannoside), α-methyl-glucoside, galactoside, ribose, xylose, arabinose, saccharate, mannitol, sorbitol, inositol, glycerol and derivatives of these monomers. The disaccharide may be exemplified by acarviosin, allolactose, cellobiose, chitobiose, galactose-alpha-1, 3-galactose, dentiobiose, isomalt, isomaltose, isomaltulose, kojibiose, lactitol, lactobionic acid, lactose, lactulose, laminaribiose, maltitol, maltose, mannobiose, melibiose, melibiulose, neohesperidose, nigerose, robinose, rutinose, sambubiose, sophorose, sucralfate, sucralose, sucrose, sucrose acetate isobutyrate, sucrose octaacetate, trehalose, truranose, xylobiose or derivatives of these disaccharides.

The further excipient may be any pharmaceutically acceptable compound which may be included or formulated in a dry powder for inhalation, in particular for delivery to the lungs, which is not an alginate oligomer, a phospholipid or an anti-adherent compound as defined herein. Many such compounds are known in the art and selecting suitable compounds to meet precise requirements would be routine for the skilled person. By way of example the further excipient maybe selected from starches, gum acacia, calcium phosphate, tragacanth, gelatine, calcium silicate, microcrystalline cellulose, polyvinylpyrrolidone, cellulose, propylene glycol, methyl cellulose, methylhydroxybenzoates, propyl hydroxybenzoates, talc, magnesium stearate, or suitable mixtures thereof. Additionally wetting agents, emulsifying agents, suspending agents, colouring agents, preserving agents, sweetening agents, flavouring agents, and the like may be used. As previously explained, the further excipient of the particles of the invention is not considered to encompass any residual solvent which may be retained following the preparation of the particles.

In certain embodiments the particles are provided in the form of a dry powder consisting essentially of said particles. In other embodiments, the particles of the invention may be provided as a part of a dry powder composition with other dry powders. Such other powders may contain one or more active agents, e.g. an antibiotic, an antifungal, an antiviral, an immunostimulatory agent, a corticosteroid, a non-steroidal anti-inflammatory drug (NSAID), a bronchodilator or a mucus viscosity reducing agent, or may be a further excipient. Representative examples of these active agents and excipients are discussed herein.

By "dry", it is meant substantially, e.g. essentially, water-free (moisture-free). This may be expressed as a water content of less than 15% w/w, e.g. less than 12%, 10%, 9%, 8%, 7%, 6%, 5%, 4.5%, 4%, 3.5%, 3%, 2.5%, 2%, 1.5% or 1% w/w as measured by weight loss on drying or chemically by the Karl Fischer method (United States Pharmacopeia; European Pharmacopoeia).

The particles of the invention, or compositions comprising the particles of the invention, may be provided in capsules or other containers, e.g. for use in inhalers. Representative capsule forming substances include but are not limited to methyl acrylate-methacrylic acid copolymers, methyl methacrylate-methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), cellulose acetate trimellitate, and sodium alginate polymer.

The invention further provides a dry powder inhaler (i.e. an inhaler device) comprising the particles of the invention, dry powder compositions comprising the particles of the invention and/or capsules comprising the same. In certain embodiments the dry powder inhaler may have a reservoir or chamber container containing the particles of the invention or dry powder compositions comprising the particles of the invention The inventors have also developed a surprisingly efficient and cost-effective spray drying process that results in high yields of the advantageous particles of the invention and which, without wishing to be bound by theory, is believed to be made possible by exploiting the particular combination of physical and chemical properties of the alginate oligomer and the selected phospholipid excipient in the particles of the invention. The anti-adherent compound may further contribute to or facilitate this combination of properties.

Specifically, the process exploits an organic-in-aqueous liquid emulsion to maximise the availability of the (limitedly water-soluble) alginate oligomer in the mixture to be spray dried and thereby reach the high levels of alginate oligomer in the particles of the invention for minimum cost of materials (in particular, the organic liquid). It is not typical to approach the use of such a co-solvent system in this way in the context of preparing spray dried particles comprising components of limited water solubility. In such contexts it is more usual to prepare an aqueous-in-organic emulsion in order to increase the concentration of the poorly water soluble components in the mixture to be spray dried. It is believed that this atypical approach of the invention is made viable on account of the electrostatic interactions that occur between the negatively charged alginate oligomer and the positively charged head groups on the phospholipid stabilising the atypical organic-in-aqueous emulsion. The anti-adherent compound may further contribute to this stabilisation effect.

Thus in a further aspect the invention provides a method for the preparation of an organic-in-aqueous liquid emulsion for spray drying so as to form the spray dried particles as defined herein, said method comprising (a) providing
    (i) an aqueous liquid composition comprising an alginate oligomer as defined herein and an aqueous liquid composition comprising an anti-adherent compound as defined herein or
    (ii) an aqueous liquid composition comprising an alginate oligomer as defined herein and an anti-adherent compound as defined herein,
(b) providing an organic liquid composition comprising a phospholipid as defined herein,
(c) combining a volume of the organic liquid composition with a volume of the aqueous liquid compositions of (i) or the aqueous liquid composition of (ii), wherein the volume of the organic liquid composition is smaller than the total volume of the aqueous liquid composition with which it is combined, and
(d) homogenising the combination so formed at any time during step (c) or on upon completion of step (c) to form the organic-in-aqueous liquid emulsion for spray drying so as to form the spray dried particles as defined herein.

It will be readily apparent that the combination so formed at any time during step (c) or on upon completion of step (c), and therefore the organic-in-aqueous liquid emulsion for spray drying, contains amounts of alginate oligomer, phospholipid and anti-adherent compound and, optionally, further excipients which upon spray drying (which process removes the aqueous and organic liquids but not the various components comprised therein) will form the spray dried particles of the invention, i.e. spray dried particles for inhalation consisting of (i) at least about 70% w/w of an alginate oligomer,
(ii) at least about 10% w/w in total of a phospholipid and an anti-adherent compound, wherein said phospholipid is solid at room temperature, and wherein said phospholipid is present at no less than 0.5% w/w and said anti-adherent compound is present at no less than 0.5% w/w, and
(iii) no greater than about 10% w/w of further excipients.

The aqueous liquid composition(s) and the organic liquid composition may be combined in a single step or a plurality of steps. The combination of the organic liquid composition and the aqueous liquid compositions may be achieved in any order. For instance, the aqueous liquid composition(s) may be added to the organic liquid composition, the organic liquid composition may be added to the aqueous liquid composition(s) or each element may be combined simultaneously. Preferably the organic liquid composition is added to one or more of the aqueous liquid composition(s).

In a further aspect there is provided an organic-in-aqueous liquid emulsion for spray drying obtained or obtainable from the above method.

The organic-in-aqueous liquid emulsion is preferably a substantially stable emulsion, by which it is meant that the emulsion will persist for at least 10 min, preferably at least 15 min, 30 min, 60 min, 120 min or 240 min following cessation of homogenisation.

In a still further aspect the invention provides a method for the preparation of the spray dried particles as defined herein, said method comprising performing the method for the preparation of an organic-in-aqueous liquid emulsion for spray drying as defined above and further (e) spray drying the organic-in-aqueous liquid emulsion formed in step (d).

In a further aspect there is provided spray dried particles obtained or obtainable from the above method.

The aqueous liquid composition comprising said alginate oligomer and/or said anti-adherent compound may be formed upon the dissolution of the alginate oligomer and/or anti-adherent compound in any pharmaceutically acceptable aqueous liquid. Conveniently this liquid will be water, preferably substantially pure water, e.g. distilled water or filtered water, however, some additional compounds (e.g. salts, organic acids, buffers) may also be present so long as such compounds are present in amounts that will not result in spray dried particles containing more than 10% of said compounds and do not interfere with particle formation. The method of the invention may include further steps of preparing the aqueous liquid composition(s). These steps may involve dissolving the alginate oligomer and/or the anti-adherent compound in the aqueous liquid at the same time or sequentially, or adding one of those two ingredients to an aqueous liquid already containing the other.

The organic liquid composition comprising said phospholipid may be formed upon the dissolution of the phospholipid in any pharmaceutically acceptable organic liquid, or organic solvent, e.g. alcohols and their derivatives (e.g. methanol, ethanol, $C_3$ alcohols and $C_4$ alcohols), ketones (e.g. acetone), acetates (e.g. ethyl acetate), halogenated solvents and their derivatives (e.g. dichloromethane, chloroform), aliphatic solvents and their derivatives (e.g. heptane, hexane, pentane). Ethanol is preferred. The selected organic liquid should have a boiling point at standard atmospheric pressure (1 atm; approximately 101325 Pa) of about 40-100° C. Substantially water miscible organic liquids may be preferable. However, some additional compounds (e.g. salts, organic acids, buffers) may also be present so long as such compounds are present in amounts that will not result in a spray dried particles containing more than 10% of said compounds and do not interfere with particle formation. The method of the invention may include further steps of preparing the organic liquid composition. These steps may involve dissolving the phospholipid in the organic liquid composition.

The further excipients of the spray dried particles of the invention, if present, may be included in the aqueous liquid composition(s) or the organic liquid composition depending on the hydrophobicity of the further excipient or provided in separate liquid compositions prior to the step of homogenisation.

Homogenisation can be achieved by any convenient means, e.g. by mechanical means and/or ultrasonic means, for example by high shear mixing. Apparatus for performing such a homogenisation (e.g. a homogeniser) is widely known and available in the art, for example a Silverson homogeniser, which may be operated at 10,000 rpm. Homogenisation is preferably performed for such time as a complete emulsion is formed to the naked eye. Homogenisation may be performed as the two liquid phases are combined, or after all of the liquid phases have been combined. In other embodiments homogenisation may begin once a part of each phase has been combined.

The volume of the organic liquid composition to be combined with, preferably added to, the aqueous liquid composition(s) must be smaller than that of the total volume of aqueous liquid composition(s). Preferably the volume of the organic liquid composition will be less than 95% that of the total volume of aqueous liquid composition(s), e.g. less than 90, 85, 80, 75, 70, 65, 60, 55, 50, 45, 40, 35, 30, 25, 20, 15, 10 or 5% that of the total volume of aqueous liquid composition(s). More preferably the volume of the organic liquid composition will be 5-70, 10-65, 15-60, 20-55, 25-50, 30-45, 35-40, 5-60, 10-55, 15-50, 20-45, 25-40, 30-35, 5-50, 10-45, 15-40, 20-35, 25-30, 5-40, 10-35, 15-30, 20-25% that of the total volume of aqueous liquid composition(s). More preferably the volume of the organic liquid composition will be about a third, e.g. 30-35% that of the total volume of aqueous liquid composition(s). In other embodiments the volume of organic liquid composition will be about 15-40%, e.g. 20-40, 20-35, or 20-30% of the total liquid volume, that is of the liquid composition that is prepared for spray drying (in other words, of the liquid composition or liquid mixture comprising the organic liquid composition and the aqueous liquid composition(s)). In another embodiment the ratio of organic liquid composition aqueous liquid composition(s) is 20-40:60-80, e.g. 20-35:65-80, 20-30:70-80 or 25:75. Thus, the method of the invention advantageously allows a reduced amount of organic liquid composition (or organic solvent to be used). The solubility of the alginate oligomer and the desired proportion of alginate oligomer in the final particles may influence the proportions of liquid compositions used. Likewise the solubility of the other ingredients and the desired proportion of those ingredients in the final particles may also influence the volume of the organic liquid composition which will be used. Similarly, the proportions of liquid compositions used must be appropriate to result in the formation of a liquid emulsion in the presence of the particle components upon homogenisation.

Spray drying can be performed using any convenient technique. The skilled man would be able to adjust his equipment and its use, e.g. the feed rate (and e.g. the inlet temperature, fan speed and pump speed, as appropriate), to ensure the particles of the invention are formed.

The methods of the invention may include further formulation and/or biological contaminant removal steps, e.g. combination with further excipients (e.g. powders) or filling into capsules and/or pasteurisation or radiation treatment. The powders of the invention may be radiolabelled, e.g. with technetium-99m, e.g. with Technegas.

The particles of the invention may be provided for use in therapy, in particular in the treatment or prevention of respiratory infections and respiratory disorders, especially disorders or conditions which involve microbial infection, in particular biofilm infection, and/or abnormal mucus, e.g. any condition associated with or characterised by defective CFTR ion channel function, COPD, COAD, COAP, bronchitis, cystic fibrosis, a medical disorder or condition associated with CF, emphysema, lung cancer, asthma or pneumonia, or a complication thereof.

A condition associated with or characterised by defective CFTR ion channel function includes conditions arising from said defective CFTR ion channel function or complications thereof. A "defective CFTR ion channel" will be understood from the above to include any defect or deficiency in CFTR function, i.e. CFTR dysfunction. Thus "a defective CFTR ion channel" effectively means, and may alternatively be expressed as, "defective CFTR ion channel function". The condition may thus be viewed as a condition associated with or characterised by or arising from CFTR dysfunction. This may include CFTR ion channels which are defective in the sense that they are non-functional or have reduced function, i.e. partially or fully lack CFTR ion channel activity (in other words in which CFTR ion channel activity is reduced or abrogated).

Defective CFTR function may arise from genetic defect or mutation or may be acquired in any other way.

The most commonly known disease associated with defective CFTR function is cystic fibrosis (CF). CF is an autosomal recessive genetic disease of humans arising from mutations in the CFTR which result stagnant mucus in all organs where mucus is formed and thickened secretions from glands in the liver and the pancreas. The presence of this stagnant mucus in the lungs, paranasal sinuses, gastrointestinal (GI) tract, pancreas, liver and female and male reproductive systems leads to a plethora of clinical conditions associated not only with poor quality of life but also morbidity and mortality. Indeed, most CF sufferers succumb to a medical disorder or condition directly associated with this stagnant mucus (also referred to in as complications of CFTR dysfunction or a medical disorder or condition associated with CF).

In some instances CFTR dysfunction is seen in subjects that have non-compound heterozygous mutant CFTR alleles. In such subjects the inherited dysfunction is mild and so is insufficient to manifest as overt CF, but is sufficient to result the plethora of clinical conditions and complications associated with overt CF.

Acquired CFTR dysfunction may arise due to environmental and/or clinical exposure, e.g. through the chronic inhalation of particulate irritants, e.g. smoke particles (tobacco, wood etc.), pollution, dust (asbestos, cotton, coal, stone, animal droppings etc.) and spores.

Accordingly, a condition associated with or characterised by a defective CFTR ion channel may include not only CF, but also other conditions involving respiratory dysfunction (more generally other respiratory disorders), and in particular disorders involving pulmonary obstruction, including particularly asthma, or respiratory disorders characterised by a chronic inflammatory state, airway remodelling and exacerbations due to respiratory tract infections. Such conditions include non-compound CFTR gene mutation heterozygosity, abnormal mucus clearance in the respiratory tract and/or breathing difficulties resulting from chronic particulate inhalation, COPD, chronic bronchitis, emphysema, bronchiectasis, asthma or chronic sinusitis, or a complication thereof.

In other embodiments the condition may be a complication, in particular a mucus-related complication, of the above-listed conditions. In a further specific embodiment the invention provides a treatment for mucus stasis and breathing difficulties in tobacco smokers and other subjects exposed to the chronic inhalation of particulate irritants, e.g. smoke particles (tobacco, wood etc.), pollution, dust (asbestos, cotton, coal, stone, animal droppings etc.) and spores.

The above discussed conditions associated with or characterised by defective CFTR ion channel function are described in greater detail in PCT/EP2015/054207, the contents of which are incorporated herein by reference.

Thus in further aspect there is provided a method for the treatment or prevention of a respiratory infection or a respiratory disorder, said method comprising administering the particles of the invention to the airways, preferably the lungs, of a subject in need thereof by inhalation.

Expressed alternatively, the invention provides a spray dried particle as defined herein for use in the treatment or prevention of a respiratory infection or a respiratory disorder, said treatment or prevention comprising administering the particles of the invention to the airways, preferably the lungs, of a subject in need thereof by inhalation.

Expressed alternatively, the invention provides the use of a spray dried particle as defined herein in the manufacture of a medicament for use in the treatment or prevention of a respiratory infection or a respiratory disorder, said treatment or prevention comprising administering the particles of the invention to the airways, preferably the lungs, of a subject in need thereof by inhalation.

The particles of the invention may be used in these aspects together with further pharmaceutical agents (i.e. therapeutic or active agents) or treatment techniques. By way of example the particle of the invention maybe used together with an antibiotic, an antifungal, an antiviral, an immunostimulatory agent, a corticosteroid, a non-steroidal anti-inflammatory drug (NSAID), a bronchodilator, a mucus viscosity reducing agent (i.e. an agent which reduces the viscosity of mucus and which terms are used interchangeably with the term "mucolytic") or a CFTR modulator (also known as a "CFTR modifier"). These agents may be administered by inhalation, e.g. in the same composition as the particles of the invention, but may also be administered by any convenient alternative route.

The antibiotic may be selected from the aminoglycosides (e.g. amikacin, gentamicin, kanamycin, neomycin, netilmicin, streptomycin, tobramycin); the β-lactams (e.g. the carbecephems (e.g. loracarbef); the 1st generation cephalosporins (e.g. cefadroxil, cefazolin, cephalexin); 2nd generation cephalosporins (e.g. cefaclor, cefamandole, cephalexin, cefoxitin, cefprozil, cefuroxime); 3rd generation cephalosporins (e.g. cefixime, cefdinir, cefditoren, cefoperazone, cefotaxime, cefpodoxime, ceftazidime, ceftibuten, ceftizoxime, ceftriaxone); 4th generation cephalosporins (e.g. cefepime); the monobactams (e.g. aztreonam); the macrolides (e.g. azithromycin, clarithromycin, dirithromycin, erythromycin, troleandomycin); the monobactams (e.g. aztreonam); the penicillins (e.g. amoxicillin, ampicillin, carbenicillin, cloxacillin, dicloxacillin, nafcillin, oxacillin, penicillin G, penicillin V, piperacillin, ticarcillin); the polypeptide antibiotics (e.g. bacitracin, colistin, polymyxin B); the quinolones (e.g. ciprofloxacin, enoxacin, gatifloxacin, levofloxacin, lomefloxacin, moxifloxacin, norfloxacin, ofloxacin, trovafloxacin); the sulfonamides (e.g. mafenide, sulfacetamide, sulfamethizole, sulfasalazine, sulfisoxazole, trimethoprim-sulfamethoxazole); the tetracyclines (e.g. demeclocycline, doxycycline, minocycline, oxytetracycline, tetracycline); the glycylcyclines (e.g. tigecycline); the carbapenems (e.g. imipenem, meropenem, ertapenem, doripenem, panipenem/betamipron, biapenem, PZ-601); other antibiotics include chloramphenicol; clindamycin, ethambutol; fosfomycin; isoniazid; linezolid; metronidazole; nitrofurantoin; pyrazinamide; quinupristin/dalfopristin; rifampin; spectinomycin; and vancomycin.

More preferably the antibiotic is selected from amikacin, gentamicin, kanamycin, neomycin, netilmicin, streptomycin, tobramycin, cefixime, cefdinir, cefditoren, cefoperazone, cefotaxime, cefpodoxime, ceftazidime, ceftibuten, ceftizoxime, ceftriaxone, cefepime, aztreonam, amoxicillin, ampicillin, carbenicillin, cloxacillin, dicloxacillin, nafcillin, oxacillin, penicillin G, penicillin V, piperacillin, ticarcillin, ciprofloxacin, enoxacin, gatifloxacin, levofloxacin, lomefloxacin, moxifloxacin, norfloxacin, ofloxacin, trovafloxacin, azithromycin, clarithromycin, dirithromycin, erythromycin, roxithromycin, telithromycin, CarbomycinA, josamycin, kitasamycin, midecamicine, oleandomycin, spiramycin, troleandromycin, tylosin, imipenem, meropenem, ertapenem, doripenem, panipenem/betamipron, biapenem, PZ-601, bacitracin, colistin, polymyxin B, demeclocycline, doxycycline, minocycline, oxytetracycline and tetracycline.

More preferably the antibiotic is selected from aztreonam, ciprofloxacin, gentamicin, tobramycin, amoxicillin, colistin, ceftazidime, azithromycin, clarithromycin, dirithromycin, erythromycin, roxithromycin, spiramycin, oxytetracycline, and imipenem.

In particularly preferred embodiments the antibiotic is selected from aztreonam, ciprofloxacin, gentamicin, tobramycin, amoxicillin, colistin and ceftazidime.

Representative antifungals include, but are not limited to the polyenes (e.g. natamycin, rimocidin, filipin, nystatin, amphotericin B, candicin; the imidazoles (e.g. miconazole, ketoconazole, clotrimazole, econazole, bifonazole, butoconazole, fenticonazole, isoconazole, oxiconazole, sertaconazole, sulconazole, tioconazole); the triazoles (e.g. fluconazole, itraconazole, isavuconazole, ravuconazole, posaconazole, voriconazole, terconazole); the allylamines (e.g. terbinafine, amorolfine, naftifine, butenafine); and the echinocandins (e.g. anidulafungin, caspofungin, micafungin).

Representative antivirals include, but are not limited to abacavir, acyclovir, adefovir, amantadine, amprenavir, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type, II interferon type I, lamivudine, lopinavir, loviride, maraviroc, moroxydine, nelfinavir, nevirapine, nexavir, oseltamivir, penciclovir, peramivir, pleconaril, podophyllotoxin, raltegravir, ribavirin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Representative immunostimulatory agents include, but are not limited to cytokines e.g. TNF, IL-1, IL-6, IL-8 and immunostimulatory alginates, such as high M-content alginates as described for example in U.S. Pat. No. 5,169,840, WO91/11205 and WO03/045402 which are explicitly incorporated by reference herein in their entirety, but including any alginate with immunostimulatory properties.

Representative NSAIDs include, but are not limited to, the salicylates (e.g. aspirin (acetylsalicylic acid), choline magnesium trisalicylate, diflunisal, salsalate, the propionic acid derivatives (e.g. ibuprofen, dexibuprofen, dexketoprofen, fenoprofen, flurbiprofen, ketoprofen, loxoprofen naproxen, oxaprozin), the acetic acid derivatives (e.g. aceclofenac, diclofenac, etodolac, indomethacin, ketorolac, nabumetone, tolmetin, sulindac), the enolic acid derivatives (e.g. droxicam, isoxicam, lornoxicam, meloxicam, piroxicam, tenoxicam), the anthranilic acid derivatives (e.g. flufenamic acid, meclofenamic acid, mefenamic acid, tolfenamic acid) and the selective COX-2 inhibitors (Coxibs; e.g. celecoxib, etoricoxib, lumiracoxib, parecoxib, rofecoxib, valdecoxib). The propionic acid derivatives (e.g. ibuprofen, dexibuprofen, dexketoprofen, fenoprofen, flurbiprofen, ketoprofen, loxoprofen naproxen, oxaprozin) are preferred, ibuprofen being most preferred.

As used herein, the terms "mucolytic agent" and "mucus viscosity reducing agent" are intended to encompass agents which reduce the intrinsic viscosity of mucus and agents which reduce the attachment of mucus to underlying epithelium, in particular agents which directly or indirectly disrupt the molecular interactions within or between the components of mucus, agents which affect the hydration of mucus and agents which modulate the ionic microenvironment of the mucosal epithelium (particularly the levels of divalent cations, e.g. calcium). Representative examples of suitable mucus viscosity reducing agents include but are not limited to a nucleic acid cleaving enzyme (e.g. a DNase such as DNase I or dornase alfa), hypertonic saline, gelsolin, a thiol reducing agent, an acetylcysteine, an uncharged low molecular weight polysaccharide (e.g. dextran, mannitol), arginine (or other nitric oxide precursors or synthesis stimulators), an agonist of the P2Y2 subtype of purinergic receptors (e.g. denufosol) or an anionic polyamino acid (e.g. poly ASP or poly GLU). Ambroxol, romhexine, carbocisteine, domiodol, eprazinone, erdosteine, letosteine, mesna, neltenexine, sobrerol, stepronin, tiopronin are specific mucolytics of note. DNase I and hypertonic saline are preferred.

Representative examples of suitable bronchodilators include but are not limited to the β2 agonists (e.g. the short-acting β2 agonists (e.g. pirbuterol, epinephrine, salbutamol, levosalbutamol, clenbuterol, terbutaline, procaterol, metaproterenol, fenoterol, bitolterol mesylate, ritodrine, isoprenaline); the long-acting β2 agonists (e.g. salmeterol, formoterol, bambuterol, clenbuterol); and the ultra-long-acting β2 agonists (e.g. indacaterol)), the anticholinergics (e.g. ipratropium, oxitropium, tiotropium) and theophylline.

Representative examples of suitable corticosteroids include but are not limited to prednisone, flunisolide, triamcinolone, fluticasone, budesonide, mometasone, beclomethasone, amcinonide, budesonide, desonide, fluocinonide, fluocinolone, halcinonide, hydrocortisone, cortisone, tixocortol, prednisolone, methylprednisolone, prednisone, betamethasone, dexamethasone, fluocortolone, aclometasone, prednicarbate, clobetasone, clobetasol, and fluprednidene.

CFTR modulators are small molecules which can redress, at least partially, a CFTR dysfunction. Present CFTR modulators fall into three main groups: CFTR potentiators, CFTR correctors and read-through agents (Derichs, N., Eur. Respir. Rev., 2013, 22(127), 58-65; Petit, R. S. and Fellner, C., Pharmacy and Therapeutics, 2014, 39(7), 500-511; the contents of which are incorporated herein by reference).

CFTR potentiators are CFTR modulators which increase the activity of the CFTR ion channel present on the epithelial cell surface. Prototypical examples of CFTR potentiators are ivacaftor (VX-770; N-(2,4-di-tert-butyl-5-hydroxyphenyl)-1,4-dihydro-4-oxoquinoline-3-carboxamide) and VRT-532 (4-methyl-2-(5-phenyl-1H-pyrazol-3-yl)-phenol) of Vertex Pharmaceuticals™)

CFTR correctors are CFTR modulators which increase the amount of CFTR protein delivered or retained at the epithelial cell surface. Prototypical examples of CFTR correctors include lumacaftor (VX-809) and VX-661 of Vertex Pharmaceuticals™ and N6022 (3-[1-(4-carbamoyl-2-methylphenyl)-5-(4-imidazol-1-ylphenyl)pyrrol-2-yl]propanoic acid).

Read-through agents (also known as "premature stop codon suppressors" (PSC suppressors) or "premature termination codon suppressors" (PTC suppressors, which terms are used interchangeably herein) are CFTR modulators which cause the translation machinery of the cell to pass over any premature termination codon in the CFTR mRNA thereby increasing the amount of substantially full length and functional CFTR produced. Prototypical examples of read-through agents include ataluren (PTC124) of PTC Therapeutics and gentamicin.

Further CFTR modulators are disclosed in WO2006002421, WO2007056341, WO2007134279, WO2009038683, WO2009064959, WO2009073757, WO2009076141, WO2009076142, WO2010019239, WO2010037066, WO2010048526, WO2010053471, WO2010054138, WO2010138484, WO2011019413, WO2011050325, WO2011072241, WO2011127241, WO2011127290, WO2011133751, WO2011133951, WO2011133953, WO2011133956, WO2011146901, Pedemonte, N., et al., J Clin Invest. 2005; 115(9):2564-2571, Van Goor, F. et al., Am J Physiol Lung Cell Mol Physiol 2006, 290: L1117-L1130, and Pedemonte, N., et al., Molecular Pharmacology, 2005 vol. 67 no. 5 1797-1807 the content of which is incorporated herein by reference.

The further pharmaceutical agent may conveniently be applied before, simultaneously with or following the particles of the invention. Conveniently the further pharmaceutical agent is applied at substantially the same time as the particles of the invention or afterwards. In other embodiments the further pharmaceutical agent may conveniently be applied or administered before the particles of the invention. The further pharmaceutical agent can also be given (e.g. administered or delivered) repeatedly at time points appropriate for the agent used. The skilled person is able to devise a suitable dosage regimen. In long term treatments the particles of the invention can also be used repeatedly. The particles of the invention can be applied as frequently as the further pharmaceutical agent, or more or less frequently.

The particles of the invention and the further pharmaceutical agent, may for example be administered together, in a single pharmaceutical formulation or composition, or separately (i.e. separate, sequential or simultaneous administration). Thus, the particles of the invention and the further pharmaceutical agent may be combined, e.g. in a pharmaceutical kit or as a combined ("combination") product.

The invention therefore also provides products (e.g. a pharmaceutical kit or a combined ("combination") product) or compositions (e.g. a pharmaceutical composition) wherein the product or composition comprises the particles of the invention as herein defined and a further pharmaceutical agent, e.g. those described above. Combinations comprising the particles of the invention and an antibiotic, an antifungal, an NSAID, a bronchodilator, a corticosteroid and/or a mucus viscosity reducing agent are preferred. Combinations comprising the particles of the invention and an antibiotic, an antifungal and/or a mucus viscosity reducing agent are especially preferred. Such pharmaceutical products and pharmaceutical compositions are preferably adapted for use in the medical methods of the invention.

The use of the particles of the invention as herein defined to manufacture such pharmaceutical products and pharmaceutical compositions for use in the medical methods of the invention is also contemplated.

Examples of suitable excipients are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Additionally lubricating agents, wetting agents, emulsifying agents, suspending agents, preserving agents, sweetening agents, flavouring agents, and the like may be used.

The subject may be any human or animal subject, but more particularly may be a human or a non-human vertebrate, e.g. a non-human mammal, bird, amphibian fish or reptile. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats and cows. Veterinary uses of the invention are thus covered. The subject may be viewed as a patient. Preferably the subject is a human.

"Treatment" when used in relation to the treatment of a medical condition/infection in a subject in accordance with the invention is used broadly herein to include any therapeutic effect, i.e. any beneficial effect on the condition or disorder or in relation to the infection/condition/disorder. Thus, not only included is eradication or elimination of the infection, or cure of the subject or infection, but also an improvement in the infection or condition or disorder of the subject. Thus included for example, is an improvement in any symptom or sign of the infection or condition or disorder, or in any clinically accepted indicator of the infection/condition/disorder. Treatment thus includes both curative and palliative therapy, e.g. of a pre-existing or diagnosed infection/condition/disorder, i.e. a reactionary treatment.

"Prevention" as used herein refers to any prophylactic or preventative effect. It thus includes delaying, limiting, reducing or preventing the condition or disorder (which reference includes infection) or the onset of the condition or disorder, or one or more symptoms or indications thereof, for example relative to the condition or disorder or symptom or indication prior to the prophylactic treatment. Prophylaxis thus explicitly includes both absolute prevention of occurrence or development of the condition or disorder, or symptom or indication thereof, and any delay in the onset or development of the condition or disorder or symptom or indication, or reduction or limitation on the development or progression of the condition or disorder or symptom or indication.

"Treatment" when used in the particular context of the treatment of a CF or a medical disorder or condition associated with CF in accordance with the invention is used broadly herein to include any therapeutic effect, i.e. any beneficial effect on CF or an associated medical disorder or condition or symptom or indicator thereof. In this section a reference to a CF-associated disorder or condition is interchangeable with a reference to a complication of CF.

As CF is a genetic disease which is characterised in each patient by the unique collection of CF-associated disorders and conditions displayed by the patient at the time of receiving the treatments of the invention, the term "treatment of CF" can be considered to be the treatment of any or all of the disorders and conditions of the patient or the treatment of a subset thereof.

Thus, although the treatments of the invention described herein do not correct the underlying genetic defect of CF, such treatments are intended to address the effects in the body which arise from the defect, e.g. an alleviation of the effects thereof, e.g. effects arising from the abnormal mucus, and includes the treatment of an associated disorder or condition and also an improvement in the clinical effects of the disorder or condition or overall well-being of the subject. In this context, a "cure" of CF would amount to complete alleviation of the various CF-associated disorders and conditions displayed by the patient at the time of receiving the treatments of the invention; however the genetic basis for the disease (the CFTR mutation) would still remain. Nonetheless, the treatments of the invention described herein do not require such a "cure" and as noted above, include an improvement in any effect which the CF has on the body. Thus included, for example, is an improvement in any symptom or sign of a CF-associated disorder or condition, or in any clinically accepted indicator of a CF-associated disorder or condition in the patient (for example, increasing mucociliary clearance in the lungs, increased responsiveness of lung infections to antibiotics, reduced incidence of constipation or improvement in nutrient absorption). In the presently claimed treatments it may be that a pre-existing CF-associated disorder or condition is not fully eradicated or the onset of a new CF-associated disorder or condition is not completely halted, but the treatments are sufficient to inhibit these processes to such an extent that the target CF-associated disorder or condition is fully resolved, or at least resolved to some extent, preferably to an extent acceptable to the subject. Treatment in these contexts thus includes both curative and palliative therapy, e.g. of a pre-existing or diagnosed CF-associated disorder or condition, i.e. a reactionary treatment.

"Prevention", when used in the particular context of the treatment of CF or a medical disorder or condition associated with CF in accordance with the invention, is used broadly herein to include any prophylactic or preventative effect in the CF patient. In this section a reference to a CF-associated disorder or condition is interchangeable with a reference to a complication of CF. "Prevention" thus includes delaying, limiting, reducing or preventing an effect of CF or a CF-associated or condition or disorder, or one or more symptoms or indications thereof, in a CF patient or the onset of CF or a CF-associated disorder or condition, or one or more symptoms or indications thereof, for example relative to the disorder, condition, symptom or indication thereof prior to the prophylactic treatment. It will be understood of course that CF in the sense of the underlying genetic defect cannot be prevented by the treatments of the present invention and this is not included. "Prevention" in these contexts thus relates to preventing an effect in the body which arises as a result of the underlying genetic defect, or as a result of the abnormal mucus.

As CF is a genetic disease which is characterised in each patient by the unique collection of CF-associated disorders and conditions displayed by the patient at the time of receiving the treatments of the invention, the term "prevention of CF or a CF-associated disorder or condition in a CF patient" can be considered to be the prevention of any CF-associated disorder or condition that the patient has yet to acquire or which the patient has acquired previously but has overcome prior to receiving the claimed treatments.

Prophylaxis explicitly includes both absolute prevention of occurrence or development of an effect of CF or a CF-associated disorder or condition, or symptom or indication thereof, and any delay in the onset or development of an effect of CF or a CF-associated disorder or condition, or symptom or indication thereof, or reduction or limitation of the development or progression of CF or a CF-associated disorder or condition, or symptom or indication thereof. The preventative treatments can also be considered as treatments that reduce the risk of a CF patient acquiring or developing CF or a CF-associated disorder or condition, or symptom or indication thereof.

The terms "patient with CF", "patient suffering from CF", "patient having CF" and "CF patient" are considered to be equivalent and are used interchangeably herein.

"Effective delivery" is taken to mean delivery of a therapeutically effective amount of alginate oligomer to the lungs, i.e. an amount of alginate oligomer that is capable of treating or preventing a respiratory infection or a respiratory disorder in which microbial infection, in particular biofilm infection, and/or abnormal mucus are involved.

EXAMPLES

Example 1—Preparation of Spray Dried Particles of the Invention

A formulation sample was prepared using compositions described in Table 1. This formulation was scaled up to contain 94 mg/ml concentration of Oligo-G (2600 Da, % G 90-95) in aqueous phase and 80% w/w in solutes concentration. Oligo-G and glycine were dissolved in water to form the aqueous phase. DPPC was dissolved in ethanol to form the organic phase. The organic phase was slowly added to aqueous phase while homogenizing at 10,000 rpm using Silverson homogenizer. After addition of all materials, the suspension formed was homogenized for further 15 minutes.

TABLE 1

Formulation composition

| COMPONENT | % | Weight (g) | % of SDP |
|---|---|---|---|
| Oligo-G | 6.491 | 106 | 80 |
| DPPC | 0.429 | 7 | 5 |
| Glycine | 1.225 | 20 | 15 |
| Ethanol | 22.964 | 375 | n/a |
| Water | 68.892 | 1125 | n/a |
| TOTAL | 100 | 1633 | 100 |

Surprisingly, a stable milky emulsion was formed which meant that the amount of ethanol used during spray drying was lowered and solute concentration increased by 3 folds. Therefore, to spray dry 1 kg of Oligo-G 10.6 L of water and only 3.5 L of ethanol is required, which means a total of only 14.1 L co-solvent was required in theory (compared to 40 L if the amounts of the co-solvents were reversed). This emulsion was used to identify spray drying parameters during scale-up and evaluate if desired geometric particle size distribution and APSD was achievable.

A pilot scale GMP spray drier (Anhydro SPX MS35, USA) was used to spray 1.6 kg of the emulsion prepared above. The powders produced were collected into a glass vial and left to stand overnight. The powders were tested for geometric particle size distribution and APSD using methods described below.

TABLE 2

Spray drying parameters

| Parameters | Experiment 11 |
|---|---|
| Process gas flow | 40 kg/hr |
| Nozzle gas flow | 14 kg/hr |
| Nozzle gas temperature | 80° C. |
| Process gas temperature | 165° C. |
| Chamber jacket temp | 100° C. |
| Cyclone jacket temp | Measured >90° C. Set = 25° C. |
| Feed rate | 60 rpm |
| Outlet temperature | Measured >90° C. |

The spray dried powder was harvested every 45 minutes to avoid clogging of the neck of the cyclone. The yield was 75% and it took 2.5 hrs to complete.

Particle size distribution was determined by laser diffractometry using a Malvern Mastersizer MicroPlus particle size analyzer (Malvern Instruments, UK). Ethyl acetate containing 2 g of SPAN 85 per litre was used as a dispersant for this experiment. The samples were prepared by dispersing around 15 mg of the powder into 3 ml of the dispersant. The equipment was turned on and the following conditions were set.

Analysis Model: Polydisperse
Presentation Code: Fraunhofer
Stirring speed: 11 o'clock (150° radius) dial position
Obscuration: 15-20%

The equipment was left for around one hour to warm up and approximately 100 ml of the dispersant was added to the sample dispersion unit. Backgrounds were first measured using the dispersant. The sample was added drop-wise into the sample dispersion unit until a suitable obscuration value was achieved. Particle size measurements were made after 5 minutes. A minimum of three measurements were made for each sample.

Aerodynamic particle size accounts for the geometric particle size, shape and density of the particle. Aerodynamic particle size distribution (APSD) is generally recognized as a critical parameter in the in vitro characterization of inhalation products since it is the APSD of an aerosol cloud that defines where the particles in that cloud are deposited following inhalation. It is generally accepted that drug-containing particles with aerodynamic particle size of less than 5 μm to be therapeutically effective and the amounts of such particles in a powder (or plurality of particles) is commonly known as FPM (fine particle mass), FPD (fine particle dose) or FPF (fine particle fraction). Particles larger than 5 μm will generally impact in the oropharynx and be swallowed.

APSD of the powder produced in this study was determined using a next generation impactor (NGI) and HPLC. The NGI contains seven stages with different cut-off diameters as shown below. FPM is determined by interpolating NGI results. However, in this study FPM is estimated as $FPM_{<4.46 \mu m}$ (i.e. particles with aerodynamic particle size of <4.46 μm) which is calculated by adding the amount of drug deposited from stage 3 to the micro orifice collector (MOC) of the NGI.

TABLE 3

NGI cut-off diameters

| Stage | Cut-off diameter at 60 LPM (μm) |
|---|---|
| 1 | 8.06 |
| 2 | 4.46 |
| 3 | 2.82 |
| 4 | 1.66 |
| 5 | 0.94 |
| 6 | 0.55 |
| 7 | 0.34 |

The device used to generate the aerosol cloud has significant influence on aerosol performance of the formulation. DPI system generally requires high dispersion energy to achieve desired powder de-agglomeration. A DPI system containing micronized powder formulation only requires higher dispersion energy compared to binary powder formulations containing coarse carriers. A high resistance device provides high dispersion energies and it was chosen for this experiment and subsequent product manufacture.

For each test, 40 mg of the spray-dried powder was filled into size 3 HPMC capsules and a high resistance (60 L) Plastiape monodose device was used to deliver the dose. The NGI method and the HPLC method are described below.

NGI

Equipment

NGI, HCP5 Copley Pump, TPK, Flow meter, Glass funnel, volumetric flasks (100 and 50 ml)

Materials

De-ionized water, Acetone, Glass microfiber filters Grade GF/A 8.1 cm

Rinsing solvent: De-Ionized Water

Preparation of Coating Solution

Weigh 100 mg Pluronic F68 into a clean 100 ml volumetric flask.

Add 3 ml of Glycerol and complete the content to volume using acetone.

Shake the content vigorously to ensure thorough mixing.

Coating

Using a suitable pipette, transfer coating solution into the NGI cups as described in Table 4

TABLE 4

Volume of coating solution added to NGI cups

| Stage cup | Coating solution (ml) |
|---|---|
| 1 | 6 |
| 2-7 | 3 |
| Micro-orifice collector (MOC) | 6 |

Tilt the cup tray gently to ensure that the liquid is covering the cups evenly, then allow to air dry.

Setting Up the NGI

Assemble the NGI according to user manual.

Add 10 mL of diluent to the cup in the pre-separator cut plate

Place a new filter in the external filter holder

Start the pump and adjust the flow rate through the impactor to 60 LPM +−3 LPM.

Check the P2 and P3 pressures and check that P3/P2 is less or equal to 0.5

Using the Critical Flow Controller, stop the airflow but do not switch off the pump Dose Dispersion Insert the Plastiape high resistance device into the mouthpiece adapter ensuring that the end of the inhaler is flush with the inner face of the mouthpiece adapter Holding the device upright, open the device and load a capsule into the chamber. Close the device Press the two buttons on the device simultaneously to pierce the capsule. The device is activated and ready to deliver.

Place the mouthpiece adapter and device onto the USP induction port

Activate the Critical Flow Controller for 4 seconds. The dose is delivered.

NGI Sample Solution Preparation

Remove the device from the mouthpiece adapter

Open the device and place the capsule into a volumetric flask. Wash the device down into the volumetric flask Remove mouthpiece from the throat and wash with a small volume of diluent into a volumetric flask Carefully remove the throat from the pre-separator and wash into the 100 ml volumetric flask, ensuring that all the internal surface is thoroughly wetted and washed Gently remove the pre-separator from the NGI and insert a stopper into the outlet Add 90 ml of diluent to the pre-separator and insert a stopper into the inlet Shake the pre-separator in a rocking, tumbling motion for two minutes. Transfer the content into a 100 ml flask. DO NOT complete to volume.

Open the NGI and add 10 ml of diluent to each cup

Gently rock the cup tray for at least two minutes. If any API can be seen remaining in the cups continue rocking the cup tray until it dissolves Vial up the sample solutions and analyze by HPLC.

TABLE 5 flask size of each NGI stage

| Samples | Flask Volume (mL) |
|---|---|
| Device and capsule | 50 |
| Mouthpiece and Throat | 100 |
| Pre-separator | 100 |
| Stage 1-MOC | 10 |

TABLE 6

HPLC parameters

| Parameter | Setting |
|---|---|
| Column | SieLC PrimeSep C 150 × 4.6 mm 5 μm 100 Å (P/N C-46.150.0510) |
| Mobile Phase | 40 mM $Na_2HPO_4$ at pH 6.0 |
| Flow Rate | 0.5 mL/min |
| Detection | Refractive Index |

TABLE 6-continued

| HPLC parameters | |
| --- | --- |
| Parameter | Setting |
| Injection Volume | 100 μL |
| Column Temp | 30° C. |
| Run Time | 5 minutes |
| Diluent | Distilled water |

The powder obtained was tested and the results are shown in Tables 7 and 8. The results demonstrate that powder-containing particles with small geometric particle size distribution that was acceptable for inhalation was obtained. This powder was characterized by acceptable FPM.

TABLE 7

| Geometrical PSD results | |
| --- | --- |
| $d_{10}$ | 1.23 |
| $d_{50}$ | 2.65 |
| $d_{90}$ | 5.20 |

TABLE 8

| NGI results | |
| --- | --- |
| Total ex-device | 22180.6 |
| FPM | 10488.7 |
| MMAD | 3.0 |
| GSD | 1.7 |
| % Emitted dose | 69 |

In the light of these results the formulation and process was considered suitable for clinical use.

Example 2—Role of Anti-Adherent Compounds on the Preparation of Spray Dried Particles of the Invention The effects of different anti-adherent agents were investigated. For this purpose, glycine and leucine were considered as potential anti-adherent agents. Suspension samples were prepared using compositions shown in Table 9. Oligo-G and/or leucine/glycine were dissolved in water to form the aqueous phase. DPPC was dissolved in ethanol to form the organic phase. The aqueous phase was slowly added to organic phase while homogenizing at 6,000 rpm using Silverson homogenizer and microfluidised as described beow.

A laboratory scale microfluidiser model M-1105 (Microfluidics Company, Newton, MA) connected to a 110 psi pneumatic supply was used in this process. The mixed material was loaded into the Microfluidiser's bulk vessel and passed through the Microfluidiser interaction chamber before being returned to the top of the bulk chamber. After every cycle/pass the equipment and the suspension was allowed to cool down before further processing. The material was processed for 5 cycles to produce microfluidised suspension.

The samples were spray dried using an inlet temperature of 120° C., a fan speed of 50 and pump speed of 10. The powders produced were collected into a glass vial and left to stand overnight.

The powders were tested for geometric particle size distribution and APSD using methods described above.

TABLE 9

| Formulation compositions | | | |
| --- | --- | --- | --- |
| Experiment | 4 | 5 | 6 |
| Oligo-G (g) | 2 | 2 | 2.25 |
| DPPC (mg) | 250 | 250 | 250 |
| Water (ml) | 25 | 25 | 25 |
| Ethanol (ml) | 75 | 75 | 75 |
| Leucine (mg) | 250 | 0 | 0 |
| Glycine (mg) | 0 | 250 | 0 |

The powder produced in Experiments 4, 5 and 6 was tested and the results are shown in Tables 10 and 11. The results demonstrate that addition of anti-adherent agent did not have any significant effect on geometric particle size distribution of the powders generated (Table 10). The results also demonstrate that addition of an anti-adherent agent improved both FPM and emitted dose (Table 11). There was only a slight difference between the formulations prepared using glycine or leucine as shown in Table 11.

TABLE 10

| Geometrical PSD results for Experiment 4, 5 and 6 | | | |
| --- | --- | --- | --- |
| Results | μm | | |
| Experiment | 4 | 5 | 6 |
| Anti-adherent agent | Leucine | Glycine | None |
| $d_{10}$ | 1.46 | 1.42 | 1.64 |
| $d_{50}$ | 3.07 | 2.86 | 3.31 |
| $d_{90}$ | 6.53 | 7.15 | 6.40 |

TABLE 11

| NGI results for Experiment 4, 5 and 6 | | | |
| --- | --- | --- | --- |
| Results | μg | | |
| Experiment | 4 | 5 | 6 |
| Anti-adherent agent | Leucine | Glycine | Non |
| Total ex-device | 29215.80 | 26593.86 | 21934.85 |
| FPM | 11084.31 | 12135.58 | 9793.81 |
| MMAD | 4.2 | 4.1 | 4.5 |
| GSD | 2.1 | 1.9 | 2.3 |
| % Emitted dose | 91 | 83 | 68 |

Example 3—Effects of Different Concentrations of DPPC on the Preparation of Spray Dried Particles of the Invention The effects of different phospholipid concentrations were investigated. Suspension samples were prepared using compositions shown in Table 12 and procedure described in Example 2. The samples were spray dried using parameters described in Example 2. The powders produced were collected into a glass vial and left to stand overnight. The powders were tested for geometric particle size distribution and APSD using methods described Example 1.

TABLE 12

| Formulation compositions | | |
|---|---|---|
| Experiment no. | 5 | 9 |
| Oligo-G (g) | 2 | 2 |
| DPPC (mg) | 250 | 125 |
| Water (ml) | 25 | 25 |
| Ethanol (ml) | 75 | 75 |
| Glycine (mg) | 250 | 375 |

The powder produced was tested and the results are shown in Tables 13 and 14. The results demonstrate that there was no significant difference in geometric particle size distribution when DPPC was reduced to 5% and glycine increased to 15% (Table 13). However, FPM was slightly reduced but this was probably due to electrostatic and it was envisaged that after powder ageing this would change as is commonly seen with DPI products.

TABLE 13

| Geometrical PSD results for Experiment 5 and 9 | | |
|---|---|---|
| Results | μm | |
| Experiment | 5 | 9 |
| % DPPC | 10 | 5 |
| % Glycine | 10 | 15 |
| $d_{10}$ | 1.42 | 1.74 |
| $d_{50}$ | 2.86 | 3.30 |
| $d_{90}$ | 7.15 | 5.99 |

TABLE 14

| NGI results for Experiment 5 and 9 | | |
|---|---|---|
| Results | μg | |
| Experiment | 5 | 9 |
| % DPPC | 10 | 5 |
| % Glycine | 10 | 15 |
| Total ex-device | 26593.86 | 28984.89 |
| FPM | 12135.58 | 10094.44 |
| MMAD | 4.1 | 4.3 |
| GSD | 1.9 | 1.9 |
| % Emitted dose | 83 | 91 |

The powders produced in Experiments 5, 9 were tested for APSD after 2 weeks product relaxation at ambient conditions and the results are shown in Table 15. The results demonstrate improved FPM deposition and this meets the 15 mg target that was set for this product

TABLE 15

| NGI results for Experiment 5 and 9 | | | | |
|---|---|---|---|---|
| Results | μg | | | |
| Time-point | Day 1 | | Two weeks | |
| Experiment | 5 | 9 | 5 | 9 |
| % DPPC | 10 | 5 | 10 | 5 |
| % Glycine | 10 | 15 | 10 | 15 |
| Total ex-device | 26593.86 | 28984.89 | 21527.19 | 26918.49 |
| FPM | 12135.58 | 10094.44 | 15604.33 | 16120.64 |
| MMAD | 4.1 | 4.3 | 2.5 | 2.8 |
| GSD | 1.9 | 1.9 | 1.8 | 1.9 |
| % Emitted dose | 83 | 91 | 67 | 84 |

Example 4—Release of OligoG from Spray Dried Particles of the Invention Upon Exposure to Saline The low amount of additives and sustained hydrophilicity of the powder of the invention enables very rapid and efficient release of the Oligo-G when exposed to liquid. This was demonstrated in an in vitro setup where the drug product prepared in Example 1 was exposed to saline, at variable concentrations and for different time periods. Approximately 60% of the Oligo-G was released after 1 min, and concentrations of 130 mg/ml, which is close to saturation, could be achieved when small amounts of fluid were applied to the dry powder.

TABLE 16

| Release of Oligo-G from spray dried particles of the invention with increasing amount if liquid added, after incubation for 1 hour | | | |
|---|---|---|---|
| Oligo-G added (mg) | Saline added (ml) | Oligo-G released (mg/ml) | Oligo-G released (%) |
| 4 | 0.015 | 129.8 | 18 |
| 4 | 0.025 | 49.2 | 25 |
| 4 | 0.04 | 75.7 | 71 |
| 4 | 0.067 | 53.8 | 85 |
| 4 | 0.1 | 39.5 | 97 |
| 4 | 0.2 | 19.7 | 99 |
| 4 | 0.4 | 9.1 | 91 |

Example 5—Preparation of Spray Dried Particles Containing High Levels of Alginate Oligomer Based on a Co-Milling Approach 4.9 g of Oligo-G was blended with 0.1 g magnesium stearate (2% w/w) using Turbula mixer set at 101 rpm for 10 minutes. The powder blend was milled using a 2" air-jet mill. The mill was operated with tangential flow, i.e. the air and powder are fed in the same direction in the milling chamber. The powder blend was fed into the mill using a Venturi feed system, where nitrogen gas was used to draw the feed material into the milling chamber. A product filter bag was affixed to the outlet of the mill, through which the grind air exhausts and the milled powder blend collects. The milling conditions were set as follows:
Grind air: Dry nitrogen gas
Grind pressure: 90 psi
Feed pressure: 85 psi
Room conditions: Ambient
No. of passes: 1

The milled powder was assessed using laser diffractometry and NGI to determine APSD, as described in Example 1. Results are summarized in Tables 17 and 18. Although the particle size results are respectable (Table 17). The APSD results (Table 18) demonstrate poor aerosol performance with only around 4 mg of Oligo-G deposited as FPM (target being 15 mg).

TABLE 17

Geometric particle size distribution results of co-milled Oligo-G-Magnesium stearate

| Percentile | Co-milled Oligo-G-Magnesium stearate particle size (μm) |
|---|---|
| $d_{10}$ | 1.93 |
| $d_{50}$ | 5.14 |
| $d_{90}$ | 9.74 |

TABLE 18

NGI results of co-milled Oligo-G-Magnesium stearate

| Stage | Results (μg) |
|---|---|
| Device | 3995.31 |
| Throat | 12284.61 |
| Pre-sep | 4238.81 |
| Stage 1 | 5226.60 |
| Stage 2 | 3719.57 |
| Stage 3 | 1399.41 |
| Stage 4 | 1054.75 |
| Stage 5 | 701.02 |
| Stage 6 | 526.60 |
| Stage 7 | 234.66 |
| MOC | 106.29 |
| Total recovery | 33487.62 |
| Total ex-device | 29492.31 |
| FPM | 4022.72 |
| % Recovery | 83.72 |

Example 6—Preparation of Spray Dried Particles Containing High Levels of Alginate Oligomer Based on a Water in Oil Emulsion Approach Dichloromethane (DCM) was selected as the organic solvent for this experiment. The formulations were prepared and spray-dried using the parameters shown in Table 19. Specifically, DPPC was dissolved in organic solvent and Oligo-G was dissolved in de-ionised water. The aqueous phase was added drop-wise into organic phase while homogenising at 6000 rpm using Silverson homogeniser. Spray-drying was performed while mixing the feed material.

TABLE 19

Formulation and processing parameters

| Components | Spray-drying parameters |
|---|---|
| Oligo-G: 4.9 g | Inlet temperature: 80° C. |
| DPPC: 100 mg | Fan speed: 50 |
| Water: 5 ml | Pump speed: 10 |
| DCM: 45 ml | |

The powders produced were collected into a glass vial and left to stand overnight. The powders were tested for geometric particle size distribution and APSD using methods described in Example 1. The powder produced following was found to be sticky and very cohesive. The geometric particle size distribution of this powder was larger than the recommended inhalation range (i.e. $d_{10}$=1.44 μm, $d_{50}$=6.18 μm, $d_{90}$=15.51 μm). It was characterised by poor aerosol performance with around 2.6 mg deposited as FPM (Table 20).

TABLE 20

NGI results for Oligo-G DPI formulation based on a water in oil emulsion approach

| Parameter | Results |
|---|---|
| Capsule fill weight (mg) | 40 |
| Ex-device dose (μg) | 26607.95 |
| FPM (μg) | 2612.13 |
| % Ex-device dose | 67 |

Example 7—Radiolabelling the of Spray Dried Particles of the Invention

The spray dried particles prepared in Example 1 were radiolabelled using the apparatus shown in FIG. 1. Briefly, Technegas generated by a Technegas Generator loaded with $^{99m}$pertechnetate (400 Mbq) [101] was drawn over a bed of dry particles (300 mg) arranged on filter paper [102] using a vacuum pump [103]. Free Technegas was trapped in 6% (w/w) EDTA solution [104].

40 mg each of dry radiolabelled or non-radiolabelled particles were filled into size 3 HPMC capsules (n=3 each). The aerodynamic size distribution of radiolabelled and non-radiolabelled particles was determined by attaching a Miat Monodose Inhaler loaded with a capsule to a multi-stage liquid impinger (MSLI; Copley Scientific, UK).

Particles deposited in the induction port (Stage 1), the four liquid stages (Stages 2 to 5) and the filter paper of Stage 6 were quantified gravimetrically. The dose of radioactivity present in each stage of the MSLI was quantified using a dose calibrator, and on one occasion using scintigraphic imaging for increased sensitivity.

Figure 2:
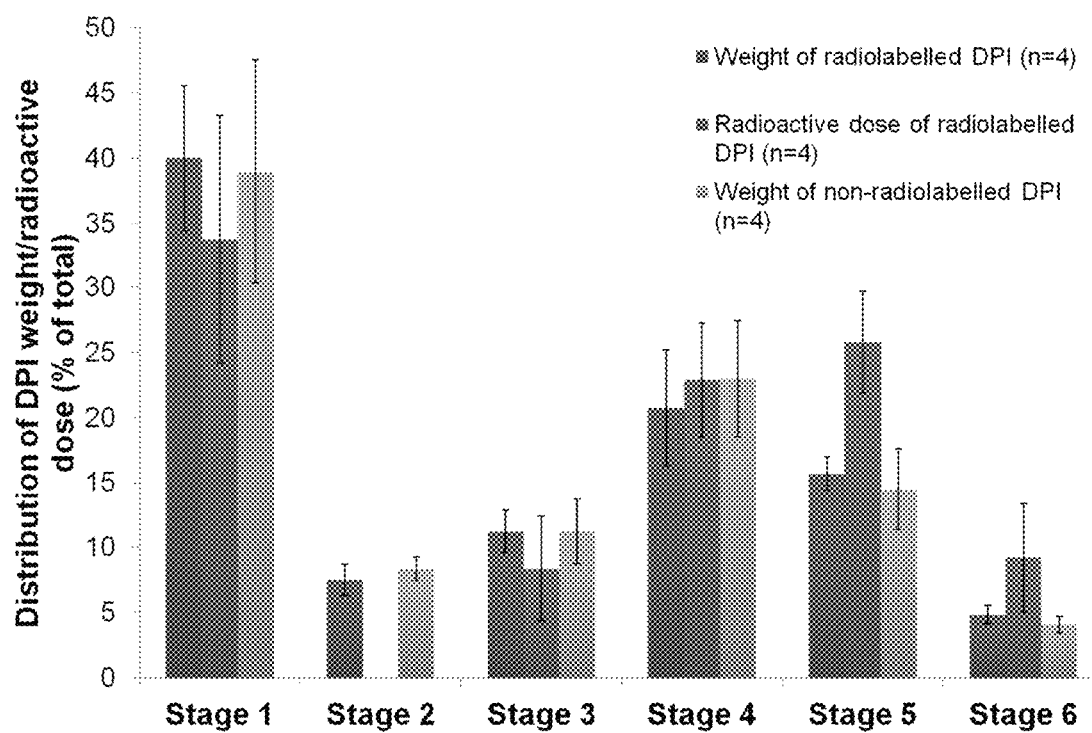
FIG. 2 shows a graphical representation of the mean distribution of weight of radiolabelled and non-radiolabelled particles as well as radioactive doses of radiolabelled particles arising from the aerodynamic size distribution analysis of Example 7. Dark grey bar (left): weight of radiolabelled particles (DPI) n=4. Medium grey bar (middle): radioactive dose of radiolabelled particles (DPI) n=4. Light grey bar (right): weight of non-radiolabelled particles (DPI) n=4.

Results show that a dry powder form of the spray dried particles of the invention can be successfully radiolabelled with an uptake of Technegas of 8.81±2.06 MBq/100 mg particles (n=4); radioactive dose was measured at time of discharging into the MSLI. FIG. 2 shows the mean % distribution of radiolabelled and non-radiolabelled particles by weight and by radioactive dose (radiolabelled particles only, measured using the dose calibrator). No radiolabel was detected by this technique in Stage 2, presumably the dose was below the detection level. Radioactive counts of this stage determined by gamma camera imaging confirmed that the % distribution was similar to the radiolabelled and non-radiolabelled particles by weight (approximately 6.8%). The distribution profiles of the three parameters measured were similar, indicating that (a) the radiolabelling process did not affect the aerodynamic properties of the particles; and (b) Technegas adhered uniformly to the particles.

This study demonstrated that the radiolabelling method employed enabled Technegas to adhere to spray dried particles of the invention without affecting aerodynamic properties, and that labelled spray dried particles of the invention will therefore provide reliable scintigraphic data on in vivo distribution once inhaled by test subjects.

Example 8—Lung Deposition of Radiolabelled Dry Powder form of the Spray Dried Particles of the Invention The primary objective of this study was to determine, using scintigraphic methods, the lung deposition of Oligo-G when administered to cystic fibrosis patients either as a nebulised solution or in a dry powder form of the spray dried particles of the invention. Secondary objectives were to determine the radiolabel distribution pattern of the two formulations in the diseased lung, including calculating the ratio of radiolabel in the central airways compared to the peripheral region (C/P index); and to characterise the extra-pulmonary deposition (i.e. oropharyngeal and stomach) of radiolabel including retention in the nebuliser or dry powder inhaler reservoir and deposition on the exhalation filter.

This study was an open label two-way randomised cross-over study in 10 cystic fibrosis patients. The subjects received a single dose of Oligo-G CF-5/20 formulated as spray dried particles of the invention (the spray dried particles of Example 1)—96 mg—delivered by three capsules via the Miat Monodose Dry Powder Inhaler, and a single dose of 1.5 mL (90 mg) aerosolised Oligo-G CF-5/20 6% solution delivered via the Sidestream Plus nebuliser, separated by a 2-14 day washout period. Each treatment was radiolabelled with 10 MBq of 99mTc in total. Technegas was drawn over a bed of DPI using a vacuum pump, allowing the Tc to adhere to the DPI without affecting its aerodynamic properties (Example 7).

Sequential anterior and posterior images of the thorax/abdomen and lateral images of the head/neck were acquired. Additionally, images of the device hardware were acquired pre- and post-dose, using a Siemens E-Cam gamma camera with a 53.3 cm field of view and fitted with a low energy high-resolution collimator.

Image analysis was performed using the WebLink software.

Lung and extra-pulmonary deposition of radiolabel including retention in the equipment were characterised. The effect of formulation (spray dried particles of the invention vs solution) on the deposition parameters was assessed using paired t-tests.

Figure 3:
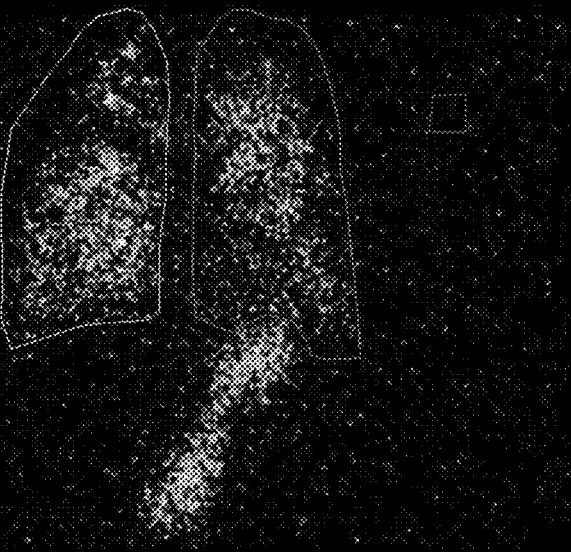
FIG. 3 shows the deposition of Oligo-G in the lungs of a CF patient following administration a nebulised solution. (A) anterior image and (B) posterior image or in the form of the spray dried particles of the invention (C) anterior image and (D) posterior image.
Figure 3:
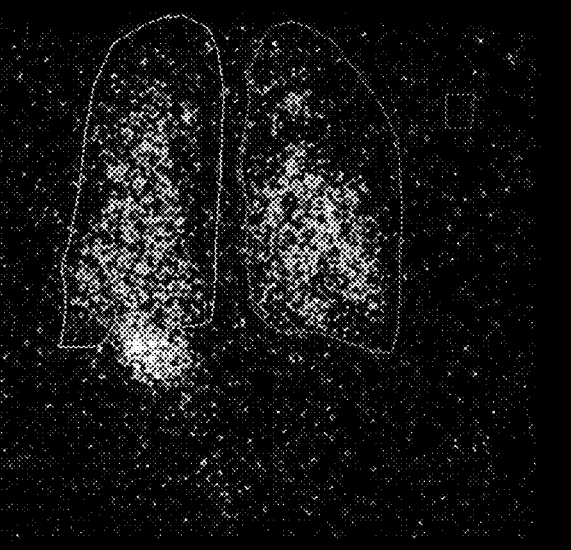
Figure 3:
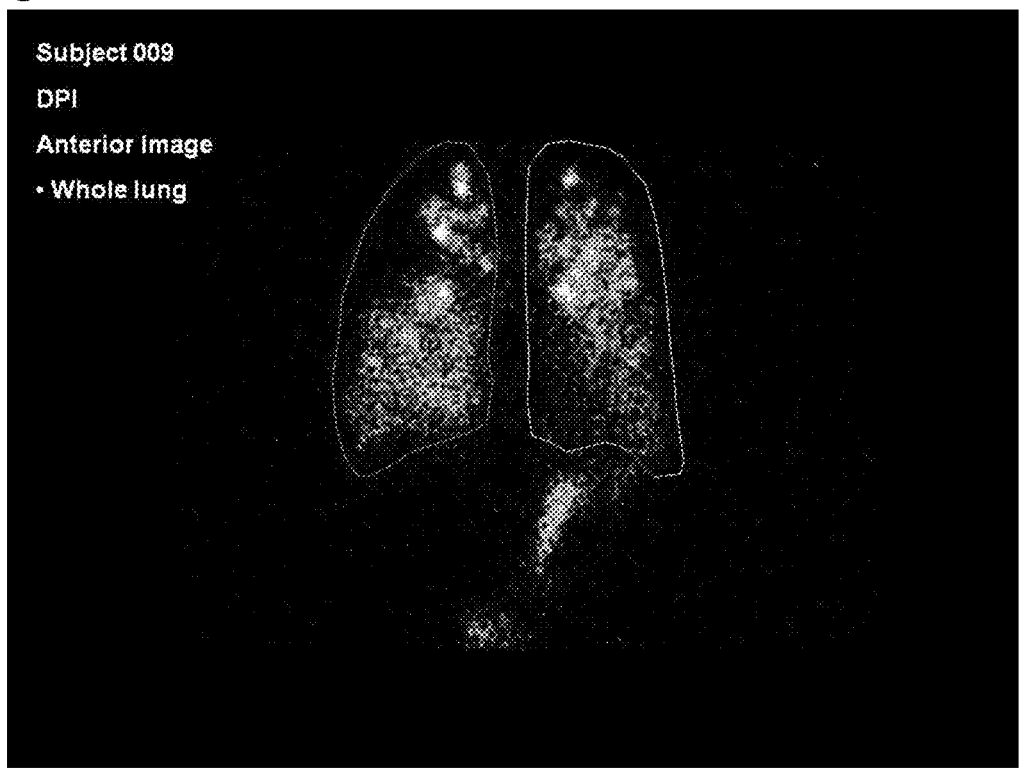
Figure 3:
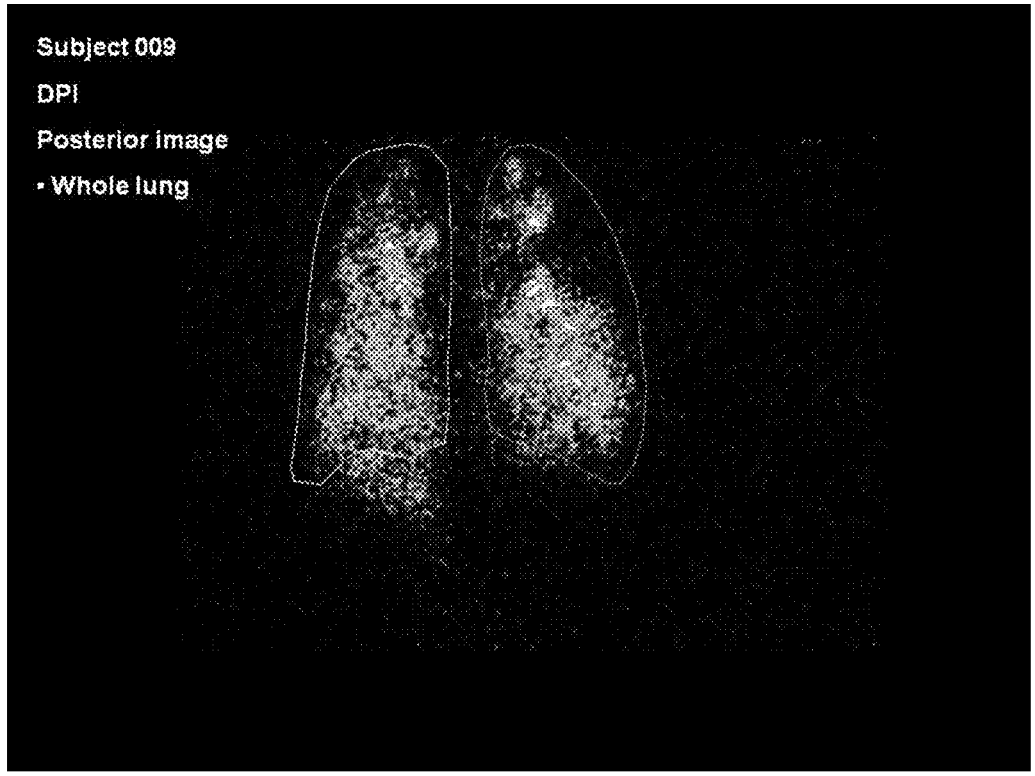
Figure 4:
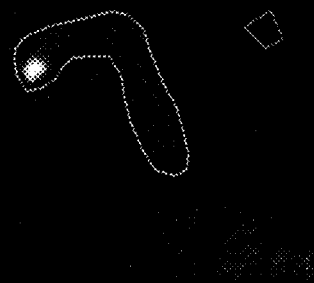
FIG. 4 shows the deposition of Oligo-G in the oropharyngeal region of a CF patient following administration a nebulised solution. (A) lateral left and (B) lateral right or in the form of the spray dried particles of the invention (C) lateral left and (D) lateral right.
Figure 4:
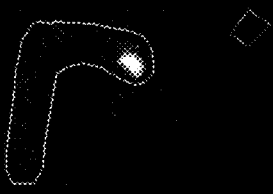
Figure 4:
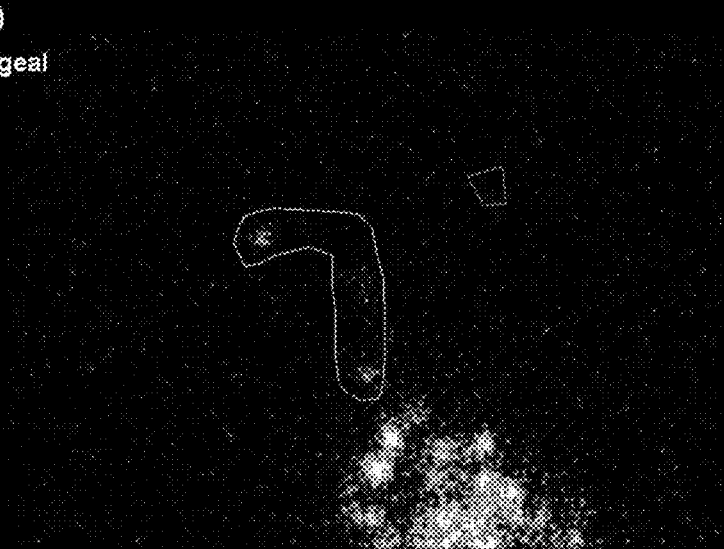
Figure 4:
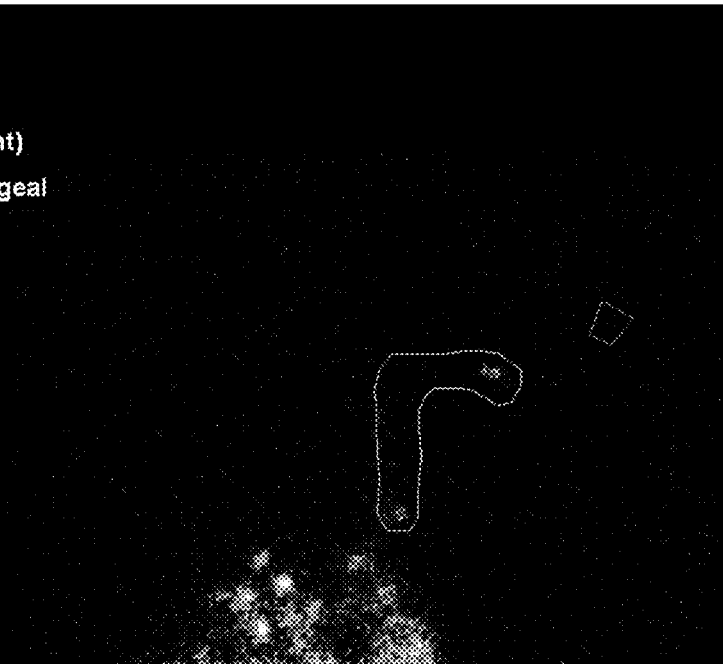

Results Showed that:
  Single dose inhalation of the spray dried particles of the invention was well tolerated
  Increased lung deposition of particles as compared to the nebulised solution (FIG. 3): Mean total radioactive counts 18,766±5,798 vs 3,982±1,277
  The lung deposition fraction of the 6% solution was calculated to be 17.3%
  The particle fraction deposited in the lung was 40.0±12.4% (n=10)
  Approximately 50±17% and 75±4% of the original dose remained in the inhalers and nebuliser respectively
  Oropharyngeal deposition (FIG. 4) was significantly higher (p=0.009) with the nebulised solution (10.1% vs 1.6%)
  The % dose in the mouth washings, that deposited in the stomach and the calculated C/P index were not significantly different between the two formulations In conclusion, significantly improved Oligo-G lung deposition (2.3 times) has been demonstrated by use of a dry powder form of the spray dried particles of the invention as compared to the 6% nebulised solution.

What is claimed is:

1. A method for the preparation of spray dried particles for inhalation, the spray dried particles for inhalation consisting of:
  at least about 70% w/w of an alginate oligomer,
  (ii) at least about 10% w/w in total of a phospholipid and an anti-adherent compound, wherein said phospholipid is solid at room temperature, and wherein said phospholipid is present at no less than 0.5% w/w and said anti-adherent compound is present at no less than 0.5% w/w, and
  (iii) no greater than about 10% w/w of further excipients, wherein said method for the preparation of said spray dried particles for inhalation comprises:
  (a) providing:
    (i) an aqueous liquid composition comprising the alginate oligomer and optionally one or more of the further excipients, and an aqueous liquid composition comprising the anti-adherent compound and optionally one or more of the further excipients, or
    (ii) an aqueous liquid composition comprising the alginate oligomer and the anti-adherent compound, and optionally one or more of the further excipients,
  (b) providing an organic liquid composition comprising the phospholipid, and optionally one or more of the further excipients,
  (c) combining a volume of the organic liquid composition with a volume of the aqueous liquid compositions of (ai), or the aqueous liquid composition of (aii), and optionally a volume of further aqueous or organic liquid compositions comprising one or more of the further excipients, wherein the total volume of the organic liquid compositions is smaller than the total volume of the aqueous liquid compositions with which it is combined, and wherein said total volume of aqueous liquid compositions and said total volume of organic liquid compositions are sufficient to provide a combination that upon being homogenized and then spray dried would form said spray dried particles for inhalation,
  (d) homogenizing the combination so formed at any time during step (c) or on upon completion of step (c) to form an organic-in-aqueous liquid emulsion for spray drying, and
  (e) spray drying the organic-in-aqueous liquid emulsion formed in step (d) to form said spray dried particles for inhalation.

2. The method of claim 1, wherein the organic liquid composition comprising the phospholipid is a solution of the phospholipid in an organic solvent selected from a group consisting of alcohols, ketones, acetates, halogenated solvents, aliphatic solvents and a combination thereof.

3. The method of claim 2, wherein the organic solvent is selected from the group consisting of methanol, ethanol, C3 alcohols, C4 alcohols, acetone, ethyl acetate, dichloromethane, chloroform, heptane, hexane, pentane and a combination thereof.

4. The method of claim 1, where the total volume of organic liquid compositions and the total volume of aqueous liquid compositions have a ratio of 20-40:60-80.

5. The method of claim 4, where the ratio of the total volume of organic liquid compositions to the total volume of aqueous liquid compositions is about 25:75.

6. The method of claim 1, wherein step (d) comprises mechanical and/or ultrasonic homogenization of the combination of the aqueous liquid compositions and organic liquid compositions.

7. The method of claim 1, wherein the organic-in-aqueous liquid emulsion is a substantially stable emulsion that will persist for at least 10 min following cessation of homogenization.

8. The method of claim 1, wherein said particles contain at least about 75% w/w of the alginate oligomer.

9. The method of claim 1, wherein said particles contain at least about 15% w/w in total of the phospholipid and the anti-adherent compound.

10. The method of claim 1, wherein said particles contain no less than 3% w/w of the phospholipid.

11. The method of claim 1, wherein said particles contain no less than 10% w/w of the anti-adherent compound.

12. The method of claim 1, wherein the relative amounts of phospholipid and anti-adherent compound present in the particles are in a ratio of 1:3.

13. The method of claim 1, wherein the relative amounts of the alginate oligomer, the phospholipid and anti-adherent compound present in the particles are in a ratio of 8:0.5:1.5.

14. The method of claim 1, wherein said particles contain essentially no further excipients.

15. The method of claim 1, wherein said particles consist of about 80% w/w of the alginate oligomer, about 15% of the w/w anti-adherent compound, and about 5% w/w of the phospholipid.

16. The method of claim 1, wherein said particles have a geometric particle size distribution in which d50 is <5 μm and d90 is <10 μm.

17. The method of claim 16 wherein the particles have a geometric particle size distribution in which d10 is <1.5 μm.

18. The method of claim 1, wherein said particles have a $FPM_{<4.46 \mu m}$ of greater than about 10 mg per 40 mg of particles.

19. The method of claim 1, wherein said particles have an emitted dose of greater than about 65%.

20. The method of claim 1, wherein the alginate oligomer has a degree of polymerization (DP), or a number average degree of polymerization (DPn) of 4 to 100.

21. The method of claim 1, wherein the alginate oligomer has at least 70% G residues.

22. The method of claim 1, wherein the alginate oligomer has a number average degree of polymerization in the range 5 to 20, a guluronate fraction ($F_G$) of at least 0.85 and a mannuronate fraction (FM) of no more than 0.15.

23. The method of claim 1, wherein the alginate oligomer has at least 70% M residues.

24. The method of claim 1, wherein the phospholipid is selected from the group consisting of phosphatidylcholines, phosphatidylethanolamines, phosphatidylglycerols, phosphatidylserines, phosphatidylinositols and a combination thereof.

25. The method of claim 1, wherein the phospholipid is selected from the group consisting of saturated phosphatidyl choline, unsaturated phosphatidyl choline, phosphatidyl ethanol amine, phosphatidyl glycerol, phosphatidyl serine, phosphatidyl inositol, dioleoylphosphatidylcholine, dimyristoyl phosphatidylcholine, dipalmitoylphosphatidylcholine (DPPC; 1, 2-Dipalmitoyl-snglycero-3-phosphocholine), distearoyl phosphatidylcholine, 1,2-Distearoyl-sn-glycero-3-phosphocholine (DSPC), diarachidoyl phosphatidylcholine, dibenoyl phosphatidylcholine, ditricosanoyl phosphatidylcholine, dilignoceroylphatidylcholine, dimiristoylphosphatidylethanolamine, dipalmitoyl-phosphatidylethanoalamine, pipalmitoleoylphosphatidylethanolamine, distearoyl-phosphatidyl ethanolamine, dimyristoylphosphatidylglycerol, dipalmitoylphosphatidyl glycerol, dipalmitolcoylphosphatidylglycerol and hydrogenated derivatives, and a combination thereof.

26. The method of claim 1, wherein the anti-adherent compound is selected from the group consisting of an amino acid, a monosaccharide, a disaccharide and a combination thereof.

27. The method of claim 26 wherein the amino acid is selected from the group consisting of leucine, isoleucine, alanine, valine, phenylalanine, lysine, glycine, and a combination thereof.

28. The method of claim 1, wherein said particles consist of
(i) about 80% w/w of an alginate oligomer, wherein said alginate oligomer has a number average degree of polymerization in the range 5 to 20, a guluronate fraction (FG) of at least 0.85 and a mannuronate fraction (FM) of no more than 0.15,
(ii) about 5% w/w of DPPC, and
(iii) about 15% w/w glycine.

29. A method for the preparation of an organic-in-aqueous liquid emulsion for spray drying so as to form spray dried particles for inhalation, the spray dried particles for inhalation consisting of
(i) at least about 70% w/w of an alginate oligomer,
(ii) at least about 10% w/w in total of a phospholipid and an anti-adherent compound, wherein said phospholipid is solid at room temperature, and wherein said phospholipid is present at no less than 0.5% w/w and said anti-adherent compound is present at no less than 0.5% w/w, and
(iii) no greater than about 10% w/w of further excipients, wherein said method for the preparation of said spray dried particles for inhalation comprises:
(a) providing:
(ai) an aqueous liquid composition comprising the alginate oligomer and optionally one or more of the further excipients, and an aqueous liquid composition comprising the anti-adherent compound and optionally one or more of the further excipients, or
(aii) an aqueous liquid composition comprising the alginate oligomer and the anti-adherent compound, and optionally one or more of the further excipients,
(b) providing an organic liquid composition comprising the phospholipid, and optionally one or more of the further excipients,
(c) combining a volume of the organic liquid composition with a volume of the aqueous liquid compositions of (ai), or the aqueous liquid composition of (aii), and optionally a volume of further aqueous or organic liquid compositions comprising one or more of the further excipients, wherein the total volume of the organic liquid compositions is smaller than the total volume of the aqueous liquid compositions with which it is combined, and wherein said total volume of aqueous liquid compositions and said total volume of organic liquid compositions are sufficient to provide a combination that upon being homogenized and then spray dried would form said spray dried particles for inhalation, and
(d) homogenizing the combination so formed at any time during step (c) or on upon completion of step (c) to form the organic-in-aqueous liquid emulsion for spray drying.

* * * * *